United States Patent [19]
Salata et al.

[11] Patent Number: 6,150,357
[45] Date of Patent: Nov. 21, 2000

[54] POTASSIUM CHANNEL AGONISTS

[75] Inventors: Joseph J. Salata, Lansdale; Jixin Wang, Wayne, both of Pa.; Michael C. Sanguinetti, Salt Lake City, Utah; Nancy K. Jurkiewicz, Spanish Fort, Ala.

[73] Assignee: Merck & Co., Inc., Rahway, N.J.

[21] Appl. No.: 09/307,685

[22] Filed: May 10, 1999

[51] Int. Cl.$^7$ .......................... A61K 31/55; A61K 31/445
[52] U.S. Cl. ............................................. 514/221; 514/320
[58] Field of Search ...................................... 514/221, 320

[56] References Cited

U.S. PATENT DOCUMENTS

| | | |
|---|---|---|
| 4,820,834 | 4/1989 | Evans et al. . |
| 5,733,905 | 3/1998 | Albright et al. . |

OTHER PUBLICATIONS

Hondeghem, L.M., Jour. of Cardiovascular Pharmacology, vol. 20 (2), S17–S–22 (1992).

Jurkiewicz, N.K. et al., Circulation Research, vol. 72 (1) (1993).

Roden, D.M., et al., Circulation, vol. 94 (8) pp. 1996–2012 (1996).

Sanguinetti, M.C. et al., Am. J. Physiol 260 (2 Part 2) E393–E399 (1991).

Sanguinetti, M.C. et al., Circulation Research, vol. 68, (1), pp. 77–84 (1991).

Sanguinetti, M.C. et al., The Jour. of General Physiology, vol. 96, pp. 195–215 (1990).

Tomaselli, G.F. et al., Circulation, vol. 90 (5) pp. 2534–2539 (1994).

*Primary Examiner*—Raymond Henley, III
*Attorney, Agent, or Firm*—Valerie J. Camara; Mark R. Daniel

[57] ABSTRACT

This application discloses a method of treating cardiac ventricular arrhythmias and repolarization abnormalities associated with long QT syndrome and/or congestive heart failure comprising the adminstration of an agonist of the slowly activating cardiac delayed rectifier potassium current ($I_{Ks}$).

12 Claims, 17 Drawing Sheets

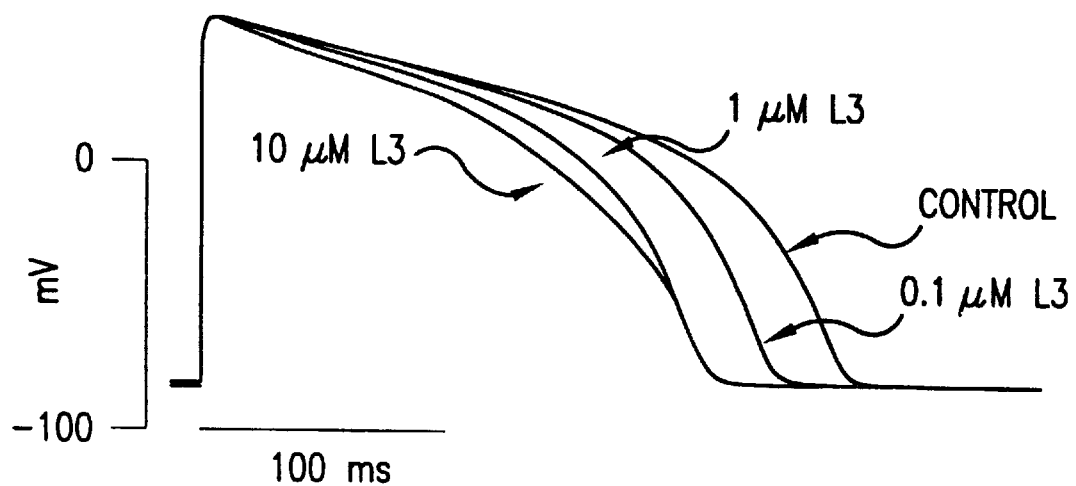
FIG.1A
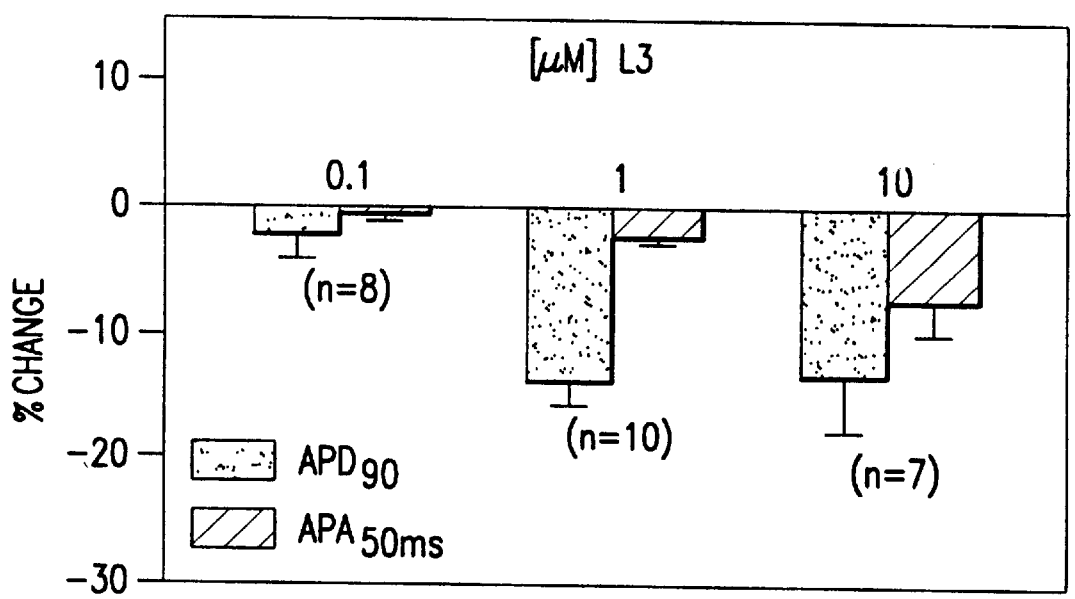
FIG.1A1

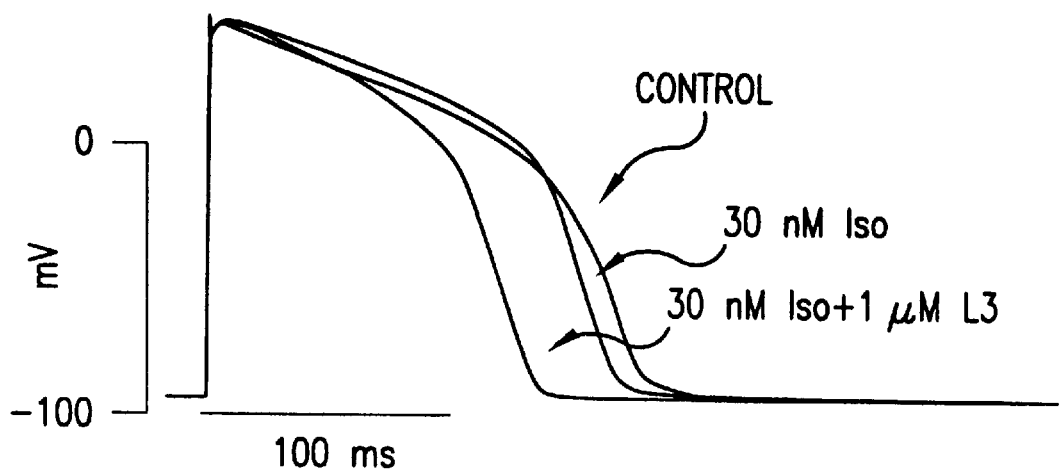
FIG.1B
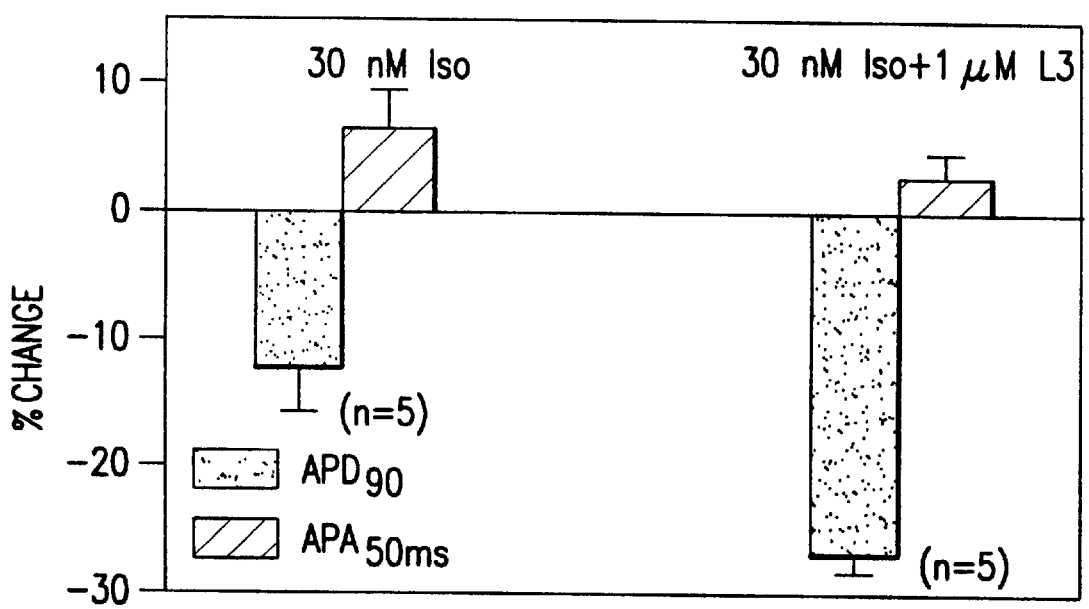
FIG.1B1

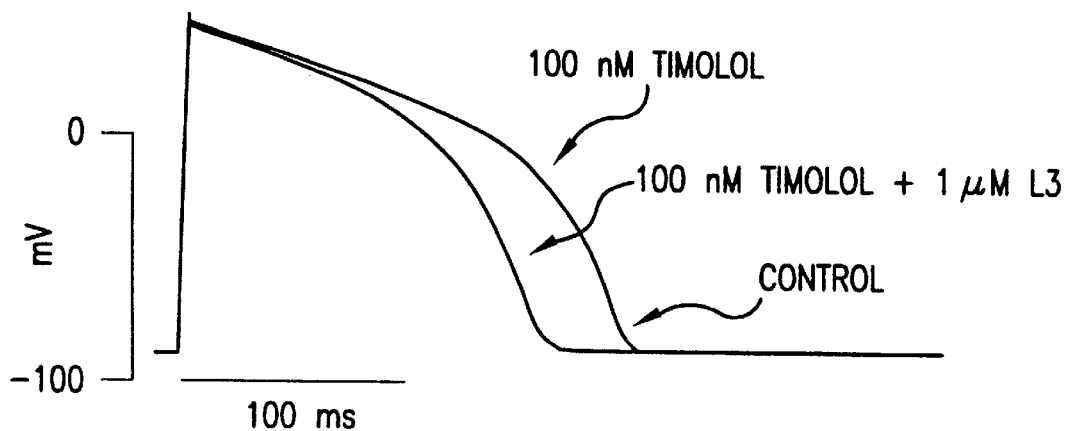
FIG.1C
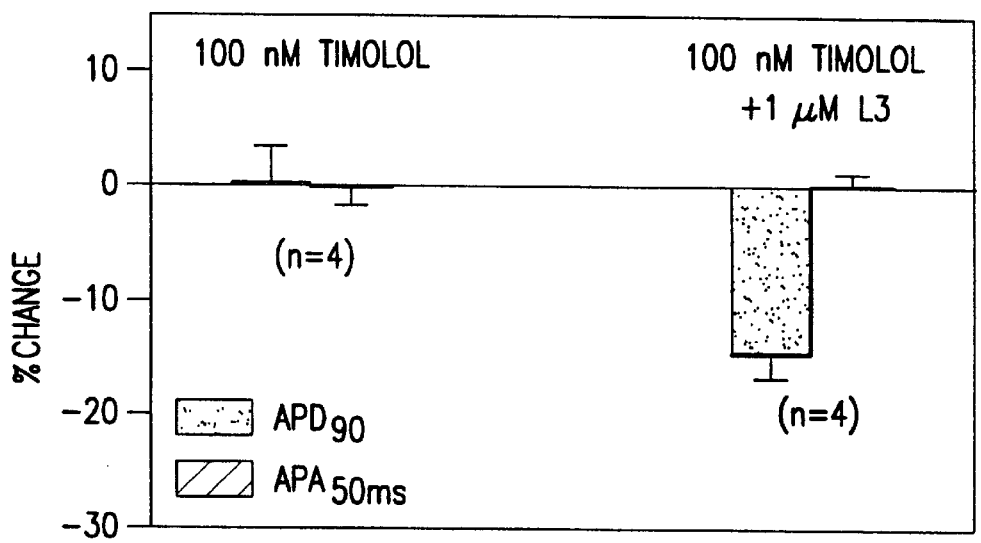
FIG.1C1

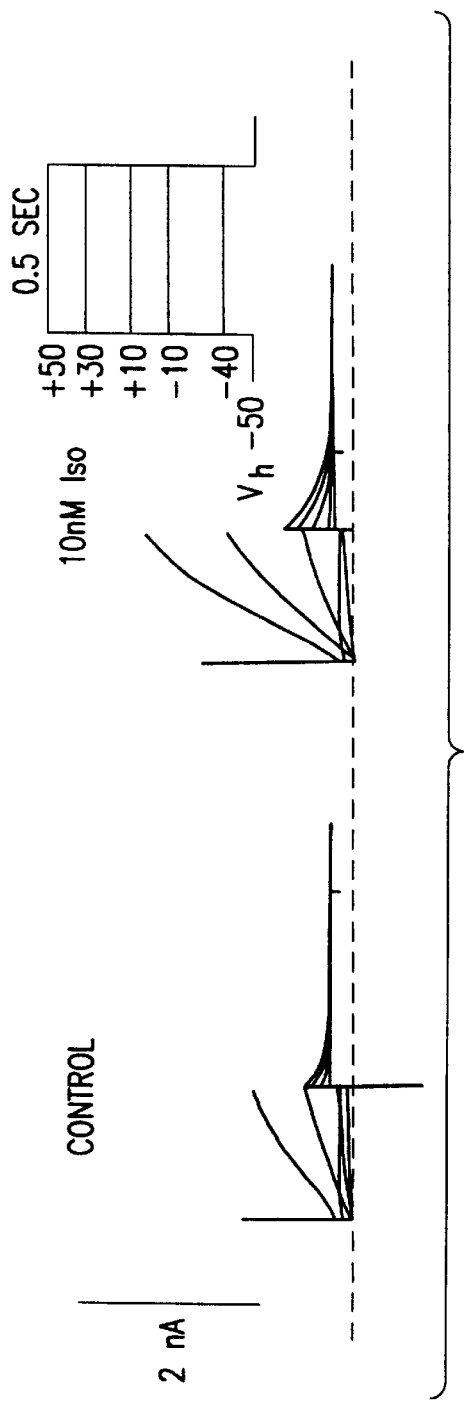
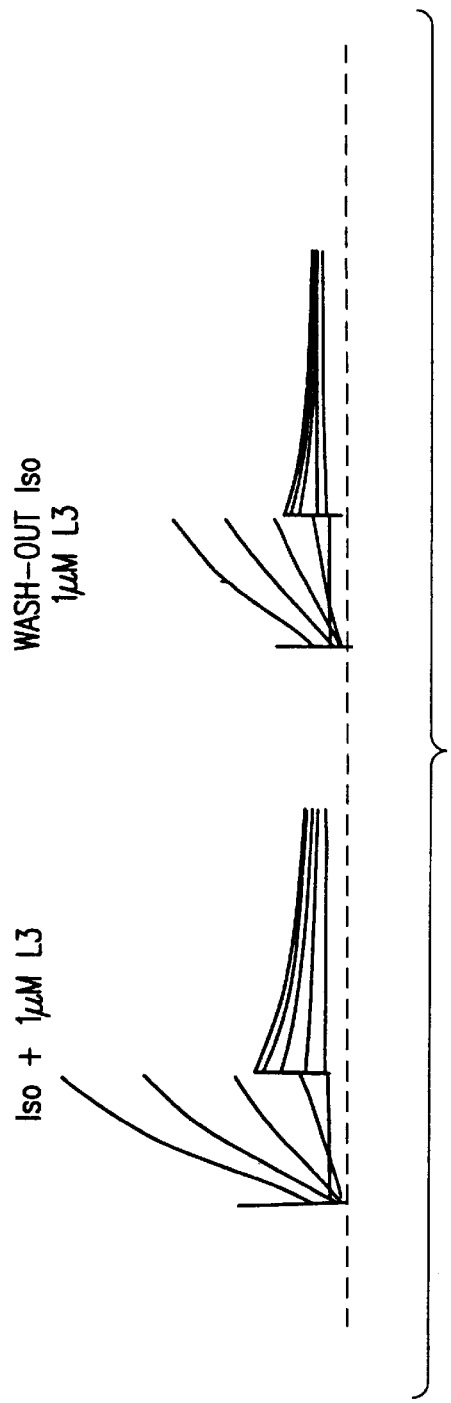
FIG.5A1
FIG.5A2

POTASSIUM CHANNEL AGONISTS

BACKGROUND OF THE INVENTION

1. Field of the Invention

This is a method of treatment of cardiac arrhythmias and repolarization abnormalities associated with long QT syndrome (LQTS) and/or congestive heart failure (CHF). This method is also useful in ameliorating or improving contractile dysfunction in CHF by hastening cardiac repolarization and relaxation and/or increasing the diastolic filling time and thereby reducing the workload of the failing heart, reducing oxygen consumption and improving cardiac performance. The method utilizes a compound that acts to enhance or activate cardiac potassium ($K^+$) channels and shorten the cardiac action potential (AP), thereby hastening repolarization, decreasing systolic contraction time and prolonging the diastolic filling time. Specific examples of compounds that act to enhance the slowly activating cardiac delayed rectifier potassium current ($I_{Ks}$) are presented. This effect of increasing the repolarizing $K^+$ current, $I_{Ks}$, causes a shortening of action potential duration (APD) that occurs as a consequence of a direct action of the compound on slowly activating cardiac delayed rectifier potassium channels in the cardiac plasma membrane underlying $I_{Ks}$, and not through an effect on other indirect pathways, such as, binding and stimulation of β-adrenergic receptors. The shortening of APD acts to prevent or reverse the electrophysiologic and contractile abnormalities that occur in LQTS and CHF, including delayed repolarization, ventricular arrhythmias, and delayed relaxation of the myocardium which compromises contractility and the pumping efficiency of the heart.

2. Description of Related Art

Cardiac arrhythmias often occur as a complication of cardiac diseases such as myocardial infarction and heart failure. Certain cardiac arrhythymias result from electrolyte imbalances, dietary deficiencies, exposure to drugs, or congenital abnormalities (Jackman W N, Friday K J, Anderson J L, Aliot E M, Clark M and Lazzara R. (1988). The Long QT syndromes: a critical review, new clinical observations and a unifying hypothesis. *Prog Cardiovasc Dis* 31: 115–172.), which produce changes in the density or regulation of various ion channels and cause abnormally long APs. In particular, aberrant cardiac repolarization, whereby APs become excessively long, predisposes patients to the risk of dangerous cardiac arrhythmias and sudden cardiac death (SCD), and is well known to occur in various acquired and genetic forms of LQTS (Roden D M, Lazzara R, Rosen M, Schwartz P J, Towbin J and Vincent G M. (1996). Multiple mechanisms in the Long-QT Syndrome; Current knowledge, gaps and future directions. *Circulation* 94: 1996–2012.), and in CHF (Tomaselli G F, Beuckelmann D J, Calkins H G, Berger R D, Kessler P D, Lawrence J H, Kass D, Feldman A M and Marban E. (1994). Suden cardiac death in heart failure. The role of abnormal repolarization. *Circulation* 90: 2534–2539.). In myocardial cells there is an ensemble of inward and outward currents that results from the flow of various inorganic ions through the cell membrane. These currents are due to the presence of selective cation and anion channels in the plasma membrane. The voltage- and time-dependent opening (activation) and closing (inactivation and/or deactivation) of these ion channels in cardiomyocytes result in the characteristically long cardiac APs (depolarization with delayed repolarization). After an initial rapid upstroke or depolarization, there is a plateau of maintained depolarization followed by repolarization to the resting membrane potential. Thus, APD is primarily responsible for the time-course of repolarization of the heart; prolongation of APD produces delays in cardiac repolarization, often manifest as an increase in the electrocardiographic QT interval. Cardiac APs also underlie a coordinated conduction of electrical impulses throughout the heart, trigger the synchronized contraction of the heart and, to some extent, control the force of the contraction. If these APs develop abnormal configuations and/or automaticity or become unsynchronized, then fatal cardiac arrhythmias can occur. As a rule, the longer the APD, the more labile is the cardiac repolarization process. This lability may be exhibited as pronounced variability or excessive prolongation in APD that can initiate or trigger early after-depolarizations (EAD) in cardiac myocytes, in vitro, which is one mechanism for induction of ventricular arrhythmias (Brugada P and Wellens H J J. (1985). Early afterdepolarizations: role in conduction block, prolonged repolarization-dependent re-excitation, and tachyarrhythmias in the human heart. *PACE* 8: 889–896; January C T and Fozzard H A. (1988). Delayed afterdepolarizations in heart muscle: Mechanisms and relevance. *Pharmacol Rev* 40: 219–227; January C T and Moscucci A. (1992). Cellular mechanisms of early afterdepolarizations. *Annal NY Acad Sci* 644: 23–32.).

Repolarization from the plateau phase of the AP in ventricular myocytes is controlled by a delicate balance between inward and outward currents in the setting of a high membrane resistance. Prolongation of APD can occur as a consequence of decreases in outward currents or increases in inward currents. Important outward currents that determine repolarization are the rapidly ($I_{Kr}$) and slowly ($I_{Ks}$) activating delayed rectifier $K^+$ currents (Sanguinetti M C and Jurkiewicz N K. (1990). Two components of cardiac delayed rectifier $K^+$ current: Differential sensitivity to block by class III antiarrhythmic agents. *J Gen Physiol* 96: 195–215.). Several class III antiarrhythmic agents selectively block $I_{Kr}$, and thereby prolong APD and the QT interval on the electrocardiogram. Excessive APD prolongation by these drugs causes acquired long QT syndrome (LQTS) that is associated with torsades de pointes, a ventricular tachyarrhythmia that can degenerate into ventricular fibrillation and cause SCD.

LQTS can also be inherited. The finding that mutations in HERG, the gene that encodes $I_{Kr}$ channels cause inherited LQTS (Curran M E, Splawski I, Timothy K W, Vincent G M, Green E D and Keating M T. (1995). A molecular basis for cardiac arrhythmia: HERG mutations cause long QT syndrome. *Cell* 80: 795–804.; Sanguinetti M C, Curran M E, Spector P S and Keating M T. (1996a). Spectrum of HERG $K^+$ channel dysfunction in an inherited cardiac arrhythmia. *Proc Natl Acad Sci USA* 93: 2208–2212.; Sanguinetti M C, Jiang C, Curran M E and Keating M T. (1995). A mechanistic link between an inherited and an acquired cardiac arrhythmia: HERG encodes the $I_{Kr}$ potassium channel. *Cell* 81: 299–307.) provided a mechanistic link between acquired LQTS and one form of inherited LQTS. The most common form of LQTS is caused by mutations in KvLQT1, a novel $K^+$ channel gene (Wang Q, Curran M E, Splawski I, Burn T C, Millholland J M, VanRaay T J, Shen J, Timothy K W, Vincent G M, de Jager T, Schwartz P J, Towbin J A, Moss A J, Atkinson D L, Landes G M, Connors T D and Keating M T. (1996). Positional cloning of a novel potassium channel gene: KvLQT1 mutations cause cardiac arrhythmias. *Nature Genetics* 12: 17–23.). Expression of KvLQT1 in either Xenopus oocytes or mammalian cell lines induced a $K^+$ current with biophysical properties unlike any known cardiac K⁺ current. Co-expression of KvLQT1 with minK induced a current that was essentially identical to cardiac $I_{Ks}$, indicating that KvLQT1 and minK proteins co-assemble to form $I_{Ks}$ channels (Barhanin J, Lesage F, Guillemare E, Fink M, Lazdunski M and Romey G. (1996). KvLQT1 and $I_{sK}$ (minK) proteins associate to form the $I_{Ks}$ cardiac potassium current. Nature 384: 78–80.; Sanguinetti M C, Curran M E, Zou A, Shen J, Spector P S, Atkinson D L and Keating M T. (1996b). Coassembly of KvLQT1 and minK ($I_{sK}$) proteins form cardiac $I_{Ks}$ potassium channel. Nature 384: 80–83.). Thus, dysfunction of either $I_{Kr}$ or $I_{Ks}$ can increase the risk of cardiac arrhythmia and SCD.

CHF is a common, highly lethal cardiovascular disorder that affects over 2 million people and claims over 200,000 lives a year in the U.S. It is estimated that ≧50% of deaths in CHF patients are sudden and that the majority of these are most likely the result of ventricular tachycardia. Myocytes isolated from failing animal and human hearts consistently exhibit a significant prolongation of APD compared with those of normal hearts, independent of the mechanism of CHF (Tomaselli, et al. (1994). Sudden cardiac death in heart failure. The role of abnormal repolarization. Circulation 90: 2534–2539.). The increase in APD in animal models and human CHF do not appear to occur as a result of alterations of the inward currents, $I_{Na}$ and $I_{Ca}$, but decreases in at least two voltage-dependent outward K⁺ currents have been consistenly observed. Both the transient outward current, $I_{to}$, and the inward rectifier K⁺ current, $I_{K1}$, have been shown to be reduced in heart failure. Recent studies have also shown that $I_{Ks}$ is decreased in animal models of heart failure and human CHF (Li G R, Sun H, Nattel, S (1998). Action potential and ionic remodelling in a dog model of heart failure. PACE 21:877; Li G R, Sun H, Feng J, Nattel, S (1998). Ionic mechanisms of th action potental prolongation in failing human ventricular cells PACE 21:877). Reductions in these outward K+currents are consistent with a prolongation of APD because they act to repolarize cardiac cells. Reductions in the rapid ($I_{Kr}$) component of the delayed rectifier K⁺ currents could also result in an increase in APD, but effects on this current in CHF remain to be determined.

In CHF reductions in outward currents during the plateau phase of the cardiac AP lead to extraordinary increases in APD predisposing the heart to ventricular arrhythmias, much like the electrophysiological changes in LQTS. For example, AP recorded from isolated ventricular myocytes obtained from human failing myocardium were very prolonged compared to those from normal hearts (Beuckelmann I) J, Näbauer M and Erdmann E. (1993). Alterations of K⁺ currents in isolated human ventricular myocytes from patients with terminal heart failure. Circ Res 73: 379–385.). This increase in APD was explained, at least partly by a decrease in $I_{to}$ as well as decreases in $I_{K1}$ and $I_{Ks}$ (Nabauer M, Beuckelmann D J and Erdmann E. (1993). Characteristics of transient outward current in human ventricular myocytes from patients with terminal heart failure. Circ. Res. 73: 386–394.); Li G R, Sun H, Feng J, Nattel, S (1998). Ionic mechanisms of th action potental prolongation in failing human ventricular cells PACE 21:877). Likewise, in canine (Kääb S, Nuss B, Chiamvimonvat N, O'Rourke B, Pak P H, Kass D A, Marban E and Tomaselli G F. (1996). Ionic mechanism of action potential prolongation in ventricular myocytes from dogs with pacing-induced heart failure. Circ Res 78: 262–273; Li G R, Sun H, Nattel, S (1998). Action potential and ionic remodelling in a dog model of heart failure. PACE 21:877) and rabbit (Rozanski G J, Xu Z, Whitney R T, Murakami H and Zucker I H. (1997). Electrophysiology of rabbit ventricular myocytes following sustained rapid ventricular pacing. J Mol Cell Cardiol 29: 721–732.) models of pacing induced-heart failure, APD of failing myocytes was statisically greater than normal controls. Similar effects on APD were evident in a renovascular hypertension-induced model of cardiac hypertrophy (Rials S J, Wu Y, Xu R A, Filart R A, Marinchak R A and Kowey P R. (1997). Regression of left ventricular hypertrophy with captopril restores normal ventricular action potetial duration, dispersion of refractoriness, and vulnerability to inducible ventricular fibrillation. Circulation 96: 1330–1336.).

Therefore, the disease states LQTS and CHF, exhibit rather similar electrophysiological abnormalities, that will be similarly responsive to pharmacological treatment. An agent or intervention that produces a decrease in APD, by causing opposing changes in the currents that underlie the increases in APD will produce a shortening of APD and thereby correct or prevent the electrophysiological abnormalities in LQTS and CHF. Pharmacological agents or other interventions that lead to an increase in outward current or a decrease in inward current will oppose prolongation of APD and therefore will be effective against arrhythmias in LQTS and CHF caused by excessive APD prolongation. For example, an activator of $I_{Kr}$ or $I_{Ks}$ channels will be useful for the treatment of LQTS that results from excessive pharmacological block of these channels, or from mutations in the genes that encode the channel proteins.

SUMMARY OF THE INVENTION

This invention relates to a method of treating cardiac ventricular arrhythmias and repolarization abnormalities associated with but not limited to acquired and genetic forms long QT syndrome and/or congestive heart failure comprising the adminstration of a therapeutically effective amount of an agonist of the slowly activating cardiac delayed rectifier potassium current ($I_{Ks}$) to patients in need of such treatment. The invention discloses 1,4-benzodiazepin-2-one and spiro[benzopyran-piperidine agonists useful in this method of treatment.

BRIEF DESCRIPTION OF THE FIGURES

FIG. 1. Effects of R-L3 on action potentials of guinea pig isolated ventricular myocytes. A-C, Action potentials were recording during stimulation at 1 Hz during control (A), and after 10 min superfusion with R-L3 at 0.1, 1 and 10 μM in normal HEPES Buffered Saline (HBS); after 30 nM Isoproterenol (Iso) alone, and following addition of 1 μM R-L3 (B); after 100 nM timolol alone and following addition of 1 μM R-L3 (C) Bar graphs show the percent changes in $APD_{90}$, and $APA_{50}$ms. Data are mean ± SEM.

DETAILED DESCRIPTION OF THE INVENTION

Figure 2A:
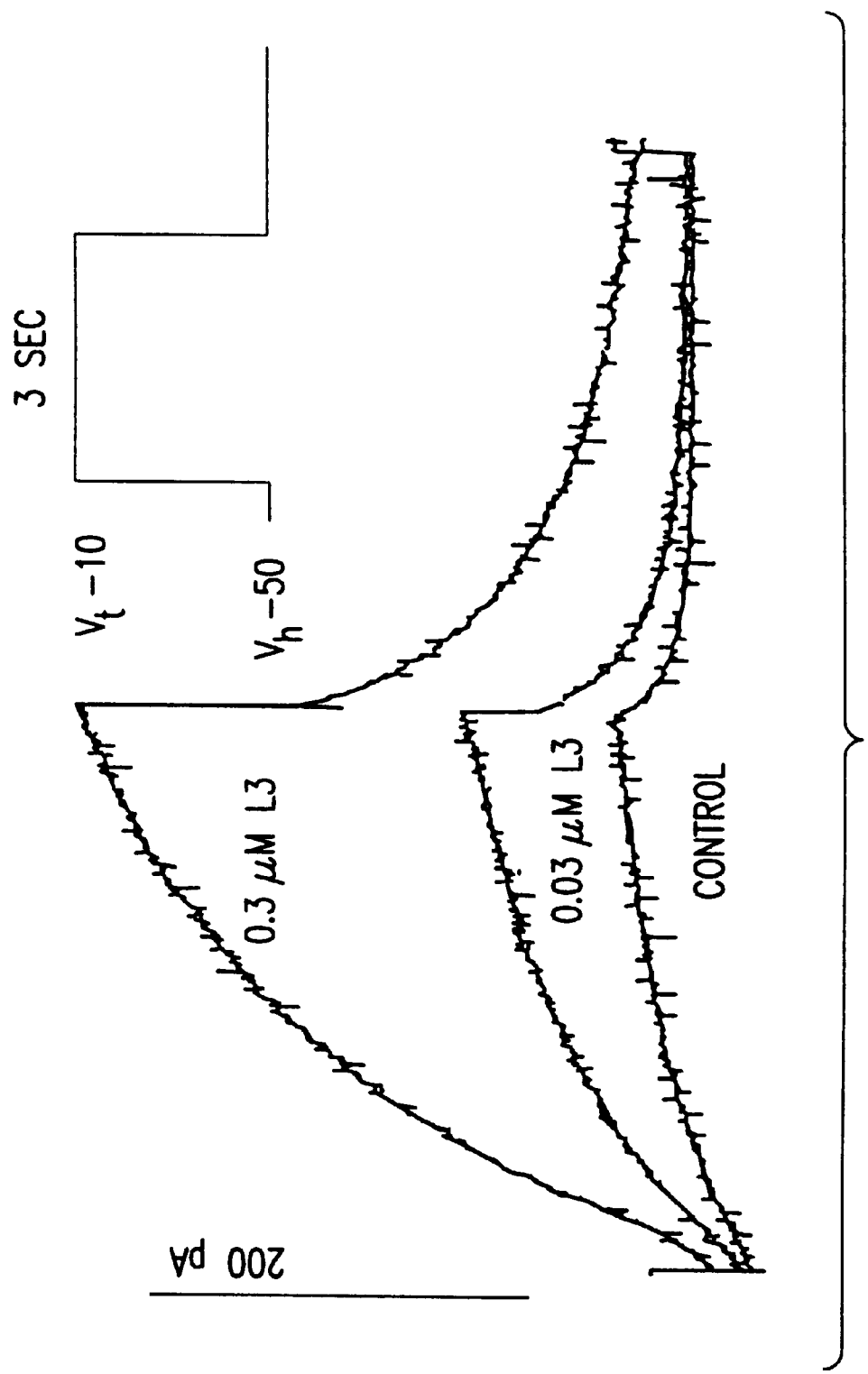
FIG. 2. Modulation of $I_{Ks}$ by R-L3 is concentration-dependent in guinea pig isolated ventricular myocytes. A, Superimposed currents from a single cell before, and after addition of 0.03 and 0.3 μM R-L3 during a 3 s voltage step from −50 to −10 mV. B, Percent increase in $I_{Ks}$ at a $V_t$ of −10 mV by R-L3 (N≧6). C, Superimposed currents before, and after addition of 10 μM R-L3 during a 7.5 s voltage step from −50 to +50 mV. D, I-V relationship for the time-dependent $I_{Ks}$ measured at the end of 7.5 s pulses (N=6).

The invention relates to a method of treating cardiac ventricular arrhythmias and repolarization abnormalities associated with but not limited to acquired and genetic forms long QT syndrome and/or congestive heart failure comprising the adminstration of a therapeutically effective amount of an agonist of the slowly activating cardiac delayed rectifier potassium current ($I_{Ks}$) to patients in need of such treatment.

An embodiment of the invention is the method as recited above, wherein the agonist of the slowly activating cardiac delayed rectifier potassium current ($I_{Ks}$) is a 1,4-benzodiazepin-2-one or a spiro[benzopyran-piperidine].

A sub-embodiment of the invention is the method as recited above, wherein the agonist of the slowly activating cardiac delayed rectifier potassium current ($I_{Ks}$) is a (3-R)-3-(1H-indol-3-ylmethyl)-1,4-benzodiazepin-2-one.

A further embodiment of this sub-embodiment is the method as recited above, wherein the 1,4-benzodiazepin-2-one agonist of the slowly activating cardiac delayed rectifier potassium current ($I_{Ks}$) is selected from the group consisting of:

(3-R)-1,3-dihydro-5-(2-fluorophenyl)-3-(1H-indol-3-ylmethyl)-1-methyl-2H-1,4-benzodiazepin-2-one;

(3-R)-1,3-dihydro-5-(2-fluorophenyl)-3-(1H-indol-3-ylmethyl)-2H-1,4-benzodiazepin-2-one;

(3-R)-7-chloro-1,3-dihydro-5-phenyl-3-(1H-indol-3-ylmethyl)-2H-1,4-benzodiazepin-2-one; and 1-methyl-5-phenyl-1'-(3-tolyl)-spiro[3H-1,4-benzodiazepine-3,4'-imidazolidine]-2(1H),2',5'-trione, or pharmaceutically acceptable salts thereof.

A sub-embodiment of the invention is the method as above wherein the agonist of the slowly activating cardiac delayed rectifier potassium current ($I_{Ks}$) is a spiro [benzopyran-piperidine].

A further embodiment of this sub-embodiment is the method as recited above, wherein the spiro[benzopyran-piperidine] agonist of the slowly activating cardiac delayed rectifier potassium current ($I_{Ks}$) is selected from the group consisting of:

N-phenyl-1'-(carboxamido)-spiro[2H-1-benzopyran-2,4'-piperidin]-4(3H)-one; and

N-(3-tolyl)-1'-(carboxamido)-spiro[2H-1-benzopyran-2,4'-piperidin]-4(3H)-one, or pharmaceutically acceptable salts thereof.

An embodiment of the invention is a method for improving contractile dysfunction in congestive heart failure patients comprising the adminstration of a therapeutically effective amount of an agonist of the slowly activating cardiac delayed rectifier potassium current ($I_{Ks}$) to patients in need of such treatment.

An embodiment of the invention is the method as recited above, wherein the agonist of the slowly activating cardiac delayed rectifier potassium current ($I_{Ks}$) is a 1,4-benzodiazepin-2-one or a spiro[benzopyran-piperidine].

A sub-embodiment of the invention is the method as recited above, wherein the agonist of the slowly activating cardiac delayed rectifier potassium current ($I_{Ks}$) is a (3-R)-3-(1H-indol-3-ylmethyl)-1,4-benzodiazepin-2-one.

A further embodiment of this sub-embodiment is the method as recited above, wherein the 1,4-benzodiazepin-2-one agonist of the slowly activating cardiac delayed rectifier potassium current ($I_{Ks}$) is selected from the group consisting of:

(3-R)-1,3-dihydro-5-(2-fluorophenyl)-3-(1H-indol-3-ylmethyl)-1-methyl-2H-1,4-benzodiazepin-2-one;

(3-R)-1,3-dihydro-5-(2-fluorophenyl)-3-(1H-indol-3-ylmethyl)-2H-1,4-benzodiazepin-2-one;

(3-R)-7-chloro-1,3-dihydro-5-phenyl-3-(1H-indol-3-ylmethyl)-2H-1,4-benzodiazepin-2-one; and 1-methyl-5-phenyl-1'-(3-tolyl)-spiro[3H-1,4-benzodiazepine-3,4'-imidazolidine]-2(1H),2',5'-trione, or pharmaceutically acceptable salts thereof.

A sub-embodiment of the invention is the method as above wherein the agonist of the slowly activating cardiac delayed rectifier potassium current ($I_{Ks}$) is a spiro [benzopyran-piperidine].

A further embodiment of this sub-embodiment is the method as recited above, wherein the spiro[benzopyran-piperidine] agonist of the slowly activating cardiac delayed rectifier potassium current ($I_{Ks}$) is selected from the group consisting of:

N-phenyl-1'-(carboxamido)-spiro[2H-1-benzopyran-2,4'-piperidin]-4(3H)-one; and

N-(3-tolyl)-1'-(carboxamido)-spiro[2H-1-benzopyran-2,
4'-piperidin]-4(3H)-one,
or pharmaceutically acceptable salts thereof.

Isolation of guinea pig ventricular myocytes. Guinea pig ventricular myocytes were isolated as described (Salata J J, Jurkiewicz N K, Wallace A A, Stupienski R F III, Guinosso P J Jr and Lynch J J Jr. (1995). Cardiac electrophysiologic actions of the histamine H$_1$-receptor antagonists astemizole and terfenadine compared with chlorpheniramine and pyrilamine. Circ Res 76: 110–119.). After isolation, the cells were stored in HEPES-buffered saline (HBS) containing (mM): 132 NaCl, 4 KCl, 1.8 CaCl$_2$, 1.2 MgCl$_2$, 10 HEPES (formal name N-2-Hydoxyethylpiperazine-N-2-ethanesulfonic acid), 10 glucose, pH=7.2, at 24–26° C. until studied, usually within 8 hours after isolation.

Action potential studies. Transmembrane potentials were recorded using conventional microelectrodes filled with 3 M KCl (tip resistances 30–50 MΩ) using an Axoclamp 2B amplifier (Axon Instruments; Foster City, Calif.) as described (Fermini B, Jurkiewicz N K, Jow B, Guinosso P J Jr, Baskin E P, Lynch J J Jr and Salata J J. (1995). Use-dependent effects of the Class III antiarrhythmic agent NE-10064 (azimilide) on cardiac repolarization: Block of delayed rectifier potassium and L-type calcium currents. J Cardiovasc Pharmacol 26: 259–271.). Cells were superfused with HBS maintained at 37° C. at a rate of 2 ml/min. APs were evoked with brief current pulses (1 ms, 1.2 times threshold) delivered at a frequency of 1 Hz through the recording electrode using an active bridge circuit. Only cells showing normal AP configurations and resting membrane potentials equal to or more negative than −85 mV were used in this study. APs were studied after a ≧5 min control period, and after ≧5 min of superfusion with each concentration of drug. After reaching a steady state effect under each condition, 20 individual APs were sampled and digitally averaged. The amplitude at 50 ms (APA$_{50}$ms) and duration at 90% repolarization (APD$_{90}$) were measured from the digitally averaged records. Concentration-response relationships were determined by measuring APs or currents in each cell under control conditions and during superfusion with successively increasing concentrations of a given drug.

Voltage-clamp of guinea pig ventricular myocytes. Whole-cell voltage-clamp studies were performed using a List EPC-7 (Medical Systems, Greenvale, N.Y.) or Axopatch 200A (Axon Instruments, Foster City, Calif.) amplifier as described (Fermini B, Jurkiewicz N K, Jow B, Guinosso P J Jr, Baskin E P, Lynch J J Jr and Salata J J. (1995). Use-dependent effects of the Class III antiarrhythmic agent NE-10064 (azimilide) on cardiac repolarization: Block of delayed rectifier potassium and L-type calcium currents. J Cardiovasc Pharmacol 26: 259–271.). Pipettes were made from square bore (1.0 mm, o.d.) borosilicate capillary tubing (Glass Co. of America, Bargaintown, N. J.). Pipettes were filled with 0.5 M K$^+$ gluconate, 25 mM KCl and 5 mM K$_2$ATP to minimize "rundown" (Giles W R and Shibata E F. (1985). Voltage clamp of bull-frog cardiac pace-maker cells: a quantitative analysis of potassium currents. J. Physiol (Lond) 368: 265–292.) and had resistances of 3 to 7 MΩ (average 5.5±0.3 MΩ). Series resistance was compensated 40–70%. Currents were low-pass filtered (−3 dB at 0.2 kHz) before digitization at 1 kHz. I$_{Ks}$ was measured during superfusion of the cells at a rate of 2–3 ml/min with normal HBS (35° C.) containing 0.4–1 μM nisoldipine to block L-type Ca$^{2+}$ current and standard selective I$_{Kr}$ blockers (e.g. 3 μM MK-499) in ~100 fold excess of their IC$_{50}$ to completely block I$_{Kr}$ (Sanguinetti M. C. and Salata J. J. (1996): Cardiac Potassium Channel Modulators: Potential for Antiarrhythmic Therapy. In: Potassium Channels and their Modulators: From Synthesis to Clinical Experience. Eds. J. M. Evans, T. C. Hamilton, S. D. Longman and G. Stemp. Taylor and Francis, London, UK). Cells were voltage clamped at a holding potential (V$_h$) of −50 mV to inactivate I$_{Na}$. Time-dependent I$_{Ks}$ amplitude was measured as the difference from the initial instantaneous current, following the settling of the capacity transient, to the final current level at the end of a depolarizing pulse. Tail current amplitude, I$_{Ktail}$, was measured as the difference from the holding current level to the peak tail current amplitude upon return to V$_h$. I$_{Ktail}$ was normalized to the maximum measured amplitude (I$_{Ktail-max}$) following 7.5 s pulses. Averaged data was fit to a Boltzmann distribution of the form: I$_{Ktail}$/I$_{Ktail-max}$=1/(1+exp[(V$_{1/2}$−V$_t$)/k]) with a nonlinear least squares fitting routine (Origin, Microcal Software, Northampton, Mass.) to estimate the half-point (V$_{1/2}$) and slope factor (k) for this relationship. The time courses of I$_{Ks}$ activation and deactivation were fit with a double exponential relationship of the form: I$_t$=A$_0$+A$_1$e$^{-t/\tau 1}$+A$_2$e$^{-t/\tau 2}$ using a Chebeshev non-iterative fitting technique (pCLAMP, Axon Instruments, Foster City, Calif.).

cRNA injection and voltage-clamp of oocytes. The isolation and maintenance of Xenopus oocytes, in vitro transcription of KvLQT1 complementary RNA (cRNA) and its injection into oocytes were performed as described previously (Sanguinetti M C, Curran M E, Zou A, Shen J, Spector P S, Atkinson D L and Keating M T. (1996b). Coassembly of KvLQT1 and minK (I$_{sK}$) proteins form cardiac I$_{Ks}$ potassium channel. Nature 384: 80–83.; Sanguinetti M C, Jiang C, Curran M E and Keating M T. (1995). A mechanistic link between an inherited and an acquired cardiac arrhythmia: HERG encodes the I$_{Kr}$ potassium channel. Cell 81: 299–307.). Stage V and VI oocytes were injected with 11.5 ng of KvLQT1 cRNA (46 nL of a 250 ng/μL solution) Currents were recorded 2 to 4 days later using standard two-microelectrode voltage clamp techniques and a Dagan TEV-200 amplifier. Oocytes were bathed at room temperature (22–25° C.) in a solution containing (mM): 94 NaCl, 2 KCl, 2 MgCl$_2$, 0.1 CaCl$_2$, 5 HEPES; pH 7.6.

Solutions. Compounds were dissolved in dimethyl sulfoxide (DMSO) at a stock concentration of 1 or 10 mM and diluted directly into test solutions. Serial dilutions were used to achieve the final test concentrations. DMSO at the concentrations used had no significant effect on any of the parameters measured in these studies. Nisoldipine was prepared as a 4 mM stock solution in DMSO and diluted as needed.

Statistics. Data are expressed as mean ± SEM (N=number of cells). Concentration-dependent changes in AP parameters and individual ionic currents were assessed by repeated-measures analysis of variance (ANOVA). Post-Hoc comparison of the treatment to the control means were made with Dunnett's t-test to determine significant changes between the control and test group means. Statistical comparisons for the time constants of I$_{Ks}$ activation and deactivation were made using a paired t-test. A one-tailed probability (p)<0.05 was considered significant.

Results. R-L3 decreases action potential duration of cardiac myocytes. R-L3 (0.1–1.0 μM) caused a concentration-dependent shortening of APD. FIG. 1A shows a representative example of APs recorded at a stimulus frequency of 1 Hz. R-L3 significantly decreased APD$_{50}$ and APD$_{90}$ without significantly affecting other parameters (Table 1). Shortening of APD was maximal at 1 μM; APD$_{90}$ was decreased at concentrations of 1 and 10 μM R-L3 by 14.2±1.6 and 13.8±4.0%, respectively.

Stimulation of β-adrenergic receptors can also shorten APD of cardiac myocytes (Carmeliet E and Vereecke J. (1969). Adrenaline and the plateau phase of the cardiac action potential. *Pflügers Arch* 313: 300–315; Sanguinetti M C, Jurkiewicz N K, Scott A and Siegl P K S. (1991). Isoproterenol antagonizes prolongation of refractory period by the Class III antiarrhythmic agent E-4031 in guinea pig myocytes. Mechanism of action. *Circ Res* 68: 77–84.). Therefore, we determined if the decrease in APD by R-L3 was mediated through the same or parallel pathway. At a concentration of 30 nM, isoproterenol (Iso) decreased $APD_{90}$ by 12.9±2.9%. Iso also increased $APA_{50ms}$ by 6.6±2.9% (FIG. 1B), presumably by enhancement of L-type $Ca^{2+}$ current (Kass R S and Wiegers S E. (1982). The ionic basis of concentration-related effects of noradrenaline on the action potential of calf cardiac Purkinje fibres. *J Physiol (Lond)* 322: 541–558.). Addition of 1 μM R-L3 in the presence of 30 nM Iso decreased $APD_{90}$ further (26.9±1.4%) and diminished the increase in $APA_{50ms}$. Block of β-adrenergic receptors with 100 nM timolol did not alter AP configuration (FIG. 1C), but prevented the effects of 30 nM Iso. In the continued presence of timolol, addition of 1 μM R-L3 decreased $APD_{90}$ by 14.6±2.2%, very similar to the effect observed as in the absence of timolol. Thus, the decrease in APD by R-L3 is additive to the effect mediated by β-adrenergic stimulation.

Figure 2B:
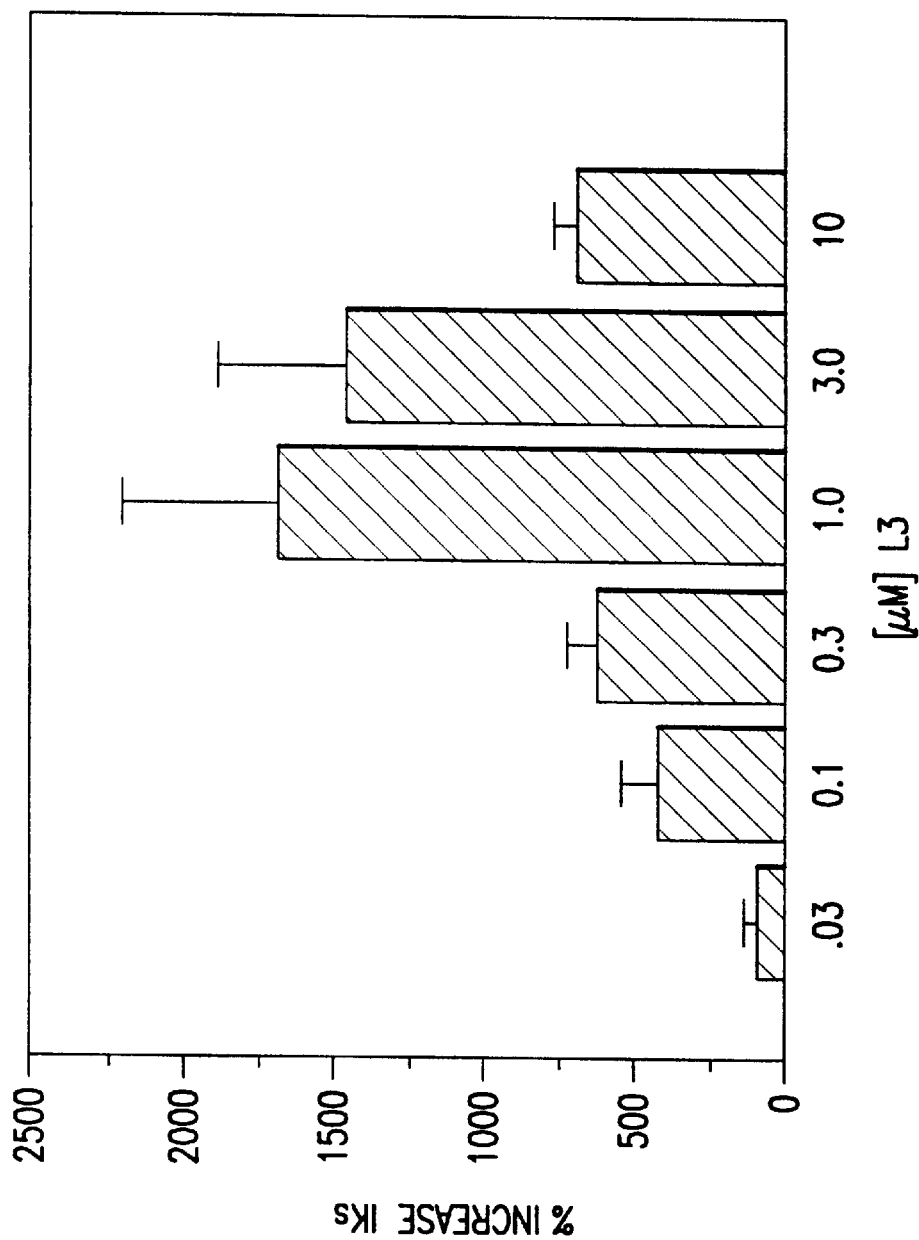
Figure 2C:
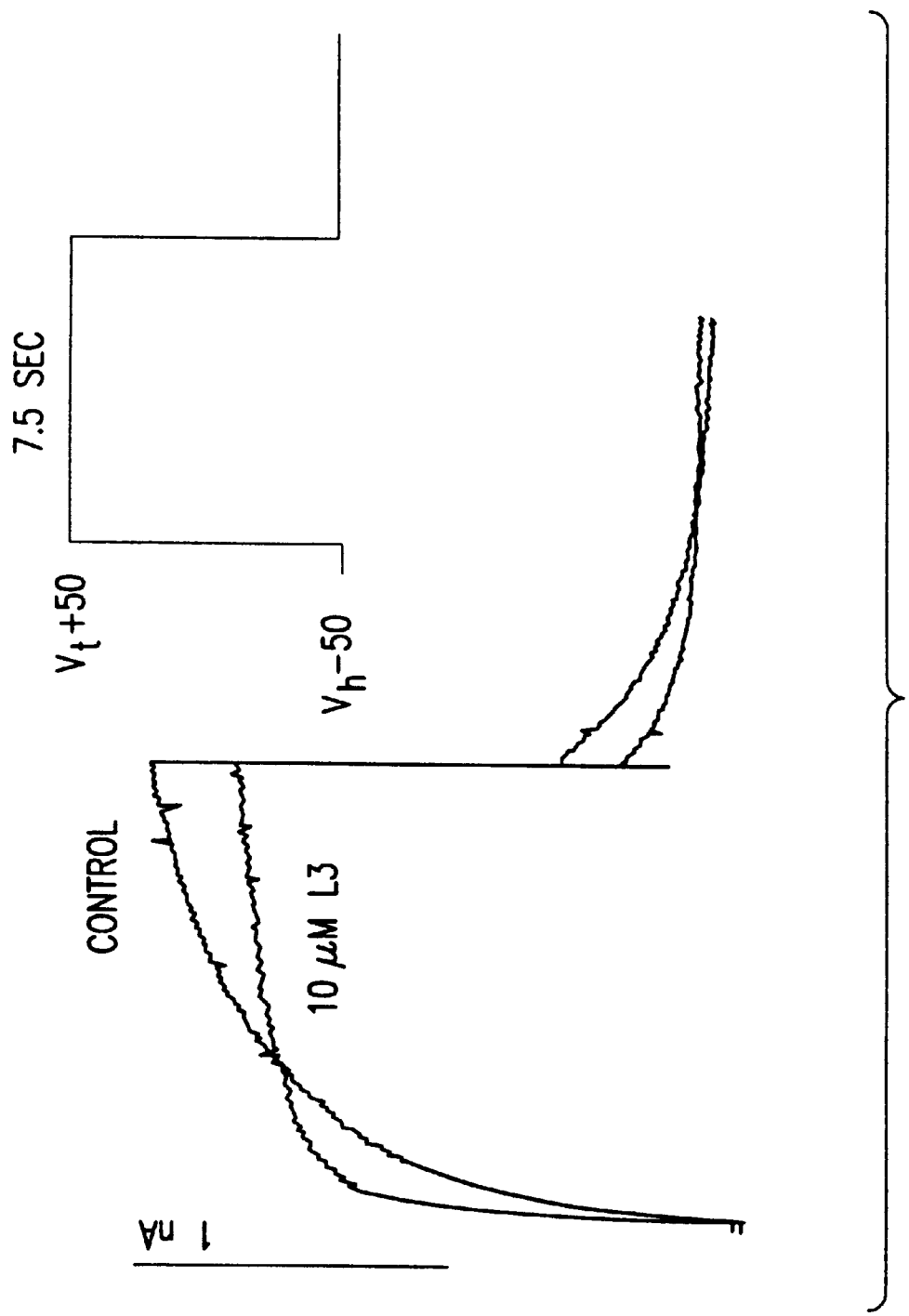
Figure 2D:
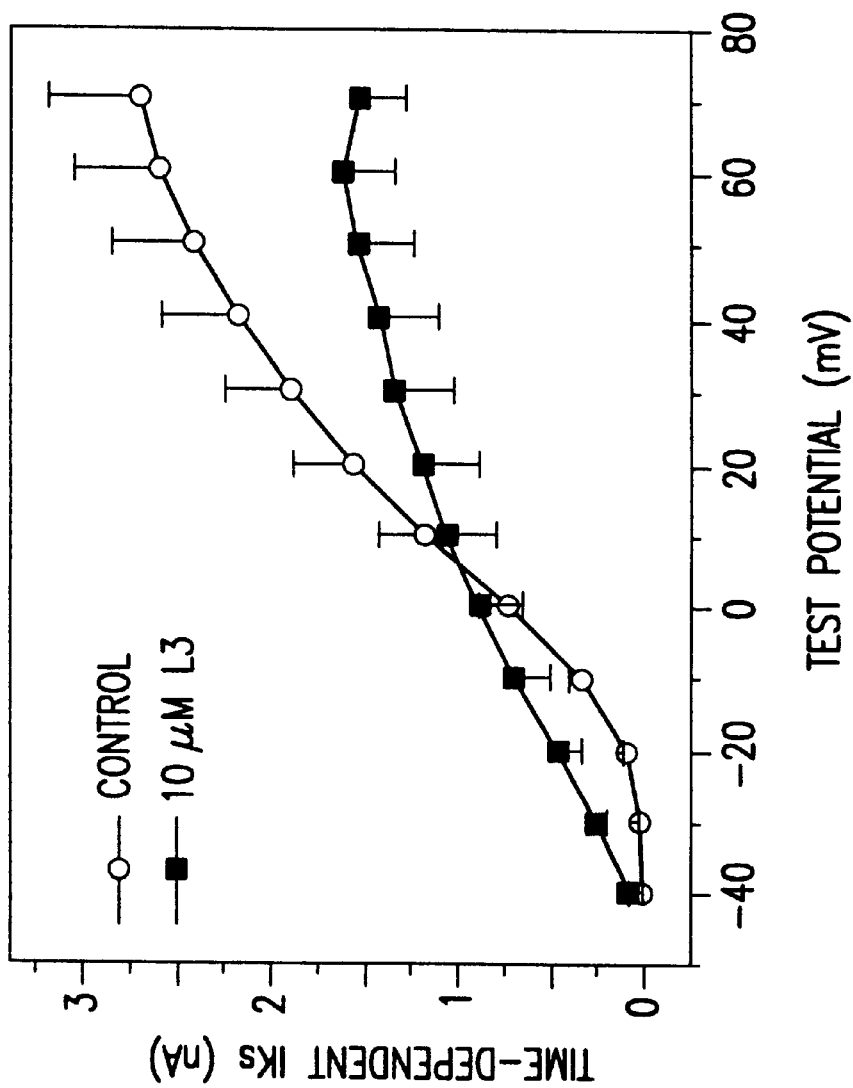
Figure 3A:
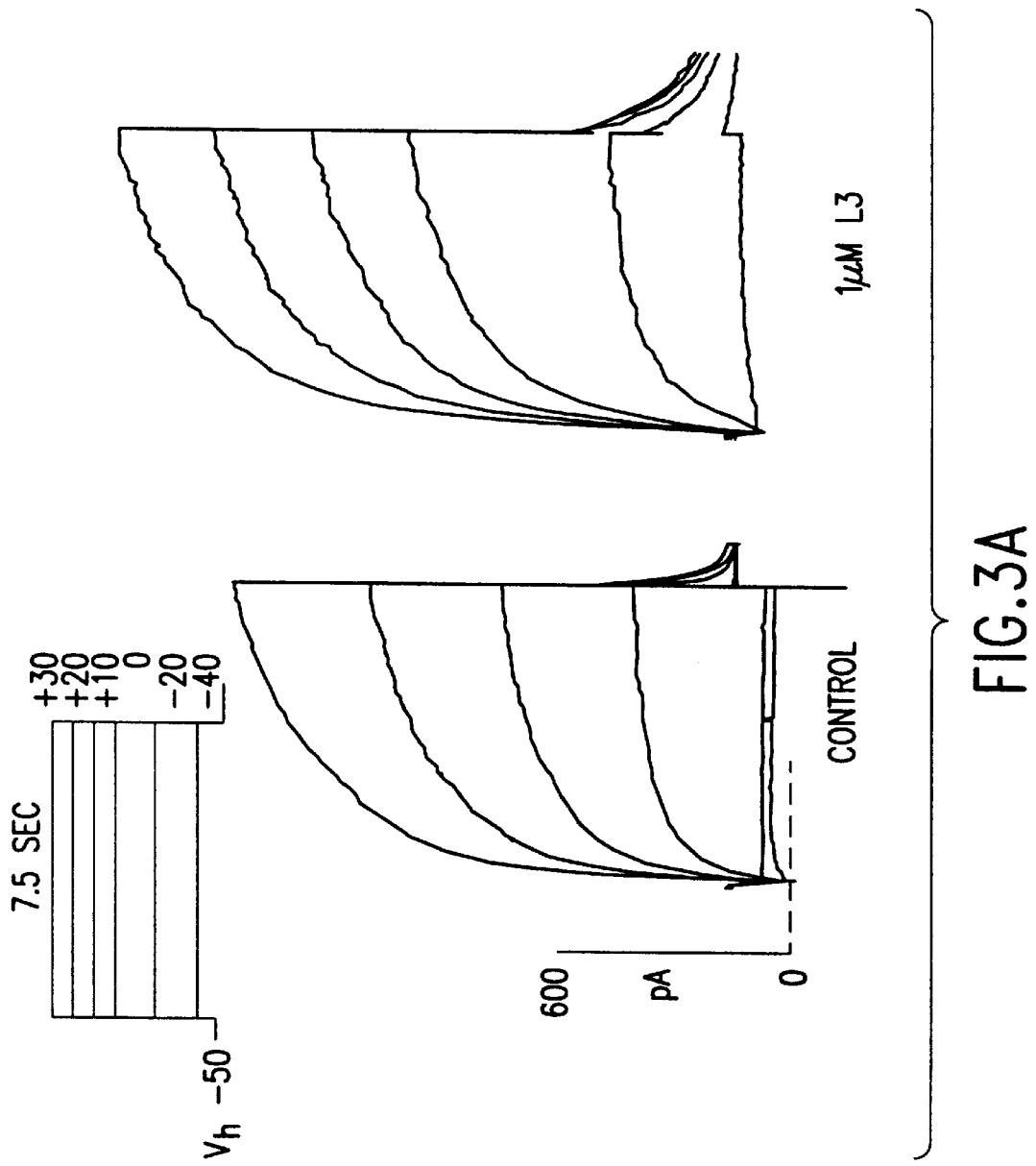
FIG. 3. R-L3 shifts the voltage-dependence of $I_{Ks}$ activation in guinea pig isolated ventricular myocytes. A, Currents recorded at the indicated $V_t$ before (control) and after addition of 1 μM R-L3. B, Isochronal activation curves were determined from the normalized amplitudes of tail currents following 7.5 s pulses. Data were fitted to a Boltzmann function to determine the $V_{1/2}$ and slope factor (k) for the relationship. The $V_{1/2}$ was 19.2±1.6 mV in control, 3.0±0.8 mV and −4.9±3.4 mV at 0.1 and 1.0 μM R-L3, respectively (N=5). The k was 11.0±1.2 mV in control and was not significantly changed by R-L3.

R-L3 increases $I_{Ks}$ of guinea pig myocytes in a concentration and stereo-specific manner. The effect of R-L3 on $I_{Ks}$ was measured under voltage-clamp conditions using 3 s depolarizations to a test potential ($V_t$) of −10 mV from a $V_h$ of −50 mV (FIG. 3A). R-L3 enhanced $I_{Ks}$ measured at −10 mV at concentrations as low as 30 nM, and had a maximal effect at 1 μM. At 30 nM, $I_{Ks}$ was increased by a factor of 17±5 (n=6). At a concentration of 3 μM or 10 μM, the % increases in $I_{Ks}$ by R-L3 were less than that observed for 1 μM (FIG. 2B). This diminished response at high concentrations was caused by a time- and voltage-dependent block of $I_{Ks}$ that was most obvious during long pulses. For example, $I_{Ks}$ was increased by 10 μM R-L3 during the first few seconds of a 7.5 s pulse to +50 mV. However, when the depolarization exceeded about 3 s, the current measured in the presence of R-L3 was reduced compared to control (FIG. 2C). R-L3 increased time-dependent $I_{Ks}$ at the end of 7.5 s pulses to potentials <+10 mV, but decreased $I_{Ks}$ at more positive potentials (FIG. 1D). Thus, the biphasic concentration-response relationship for the effects of R-L3 on $I_{Ks}$ for 3 s pulses to −10 mV (FIG. 2B) reflects the dual effects of the drug: activation that predominates at low concentrations and voltage-dependent block at higher concentrations.

The increase of $I_{Ks}$ by R-L3 was stereo-specific. S-L3 blocked $I_{Ks}$ at all concentrations (1 to 10 μM) and test potentials (−10 to +50 mV) examined. At concentrations of 1 and 10 μM, S-L3 blocked $I_{Ks}$ measured at the end of a 1-s test pulse to +50 mV, by an average of 14.8±4.3% and 68.8±3.4% (N=5).

Figure 3B:
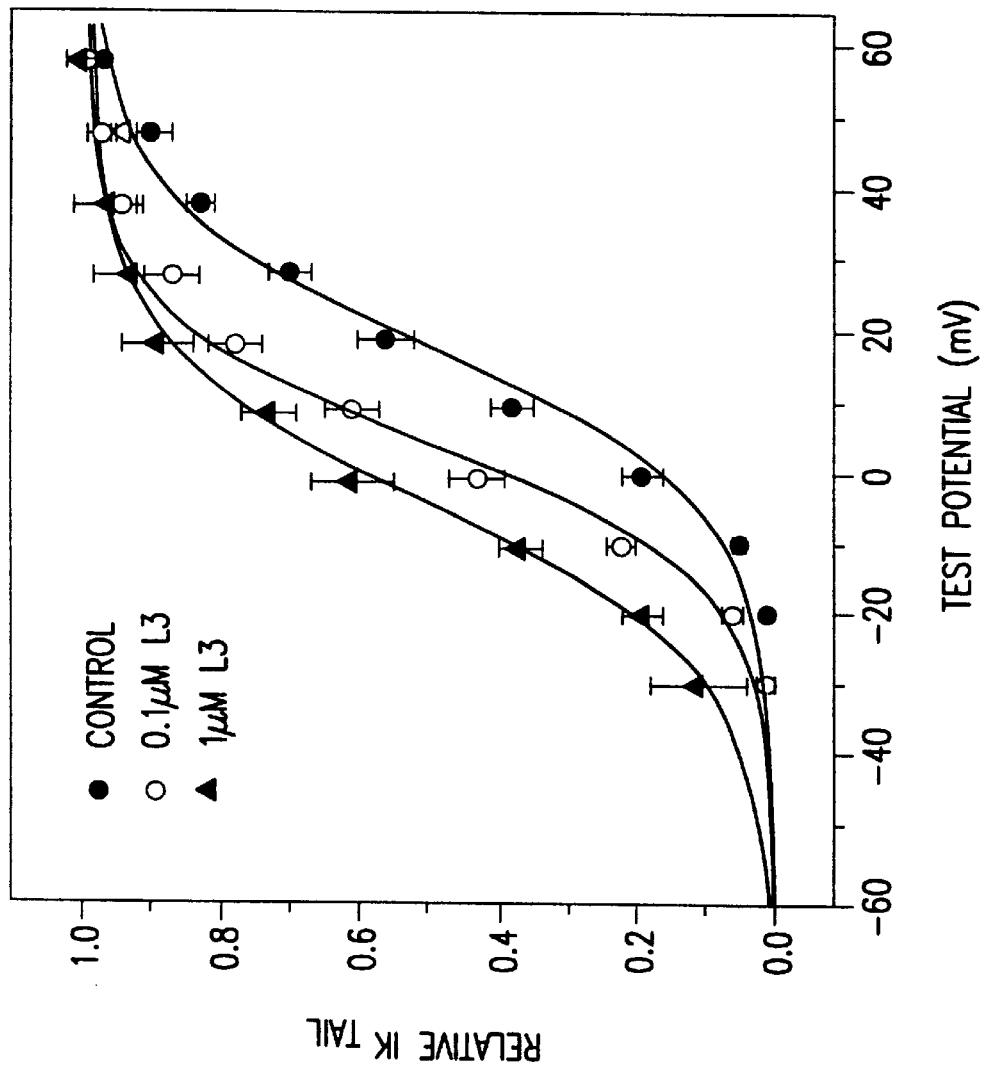

R-L3 shifts the voltage dependence of activation and slows deactivation of $I_{Ks}$. The voltage dependence of $I_{Ks}$ activation was estimated using 7.5 s depolarizing steps from a $V_h$ of −50 mV (FIG. 3A). The amplitude of the tail currents was normalized relative to the maximum amplitude and fit to a Boltzmann function (FIG. 3B). Because $I_{Ks}$ does not achieve a steady state, even during extremely long pulses (Hice R E, Folander K, Salata J J, Smith J S, Sanguinetti M C and Swanson R. (1994). Species variants of the $I_{sK}$ protein: differences in kinetics, voltage dependence, and $La^{3+}$ block of the currents expressed in Xenopus oocytes. *Pflügers Arch* 426: 139–145.) the activation curves are isochronal. In control, the $V_{1/2}$ was 19.2±1.6 mV and k for this relationship was 11.0±1.2 mV (N=5). In these same cells, R-L3 shifted $V_{1/2}$ to 3.0±0.8 mV at 0.1 μM −4.9±3.4 mV at 1 μM, but had no effect on k. The maximally activated $I_{Ks}$ measured at a $V_t$ of +60 mV (896±196 vs. 953±183 pA, 1 μM) was slightly but not significantly increased by R-L3. Likewise, following pretreatment with 100 nM timolol, 1 μM R-L3 shifted the $V_{1/2}$ by −19 mV without affecting k, indicating that its effect was independent of β-adrenergic stimulation. These results suggest that the primary mechanism of the increase in $I_{Ks}$ by R-L3 is an effect on channel gating.

Figure 4:
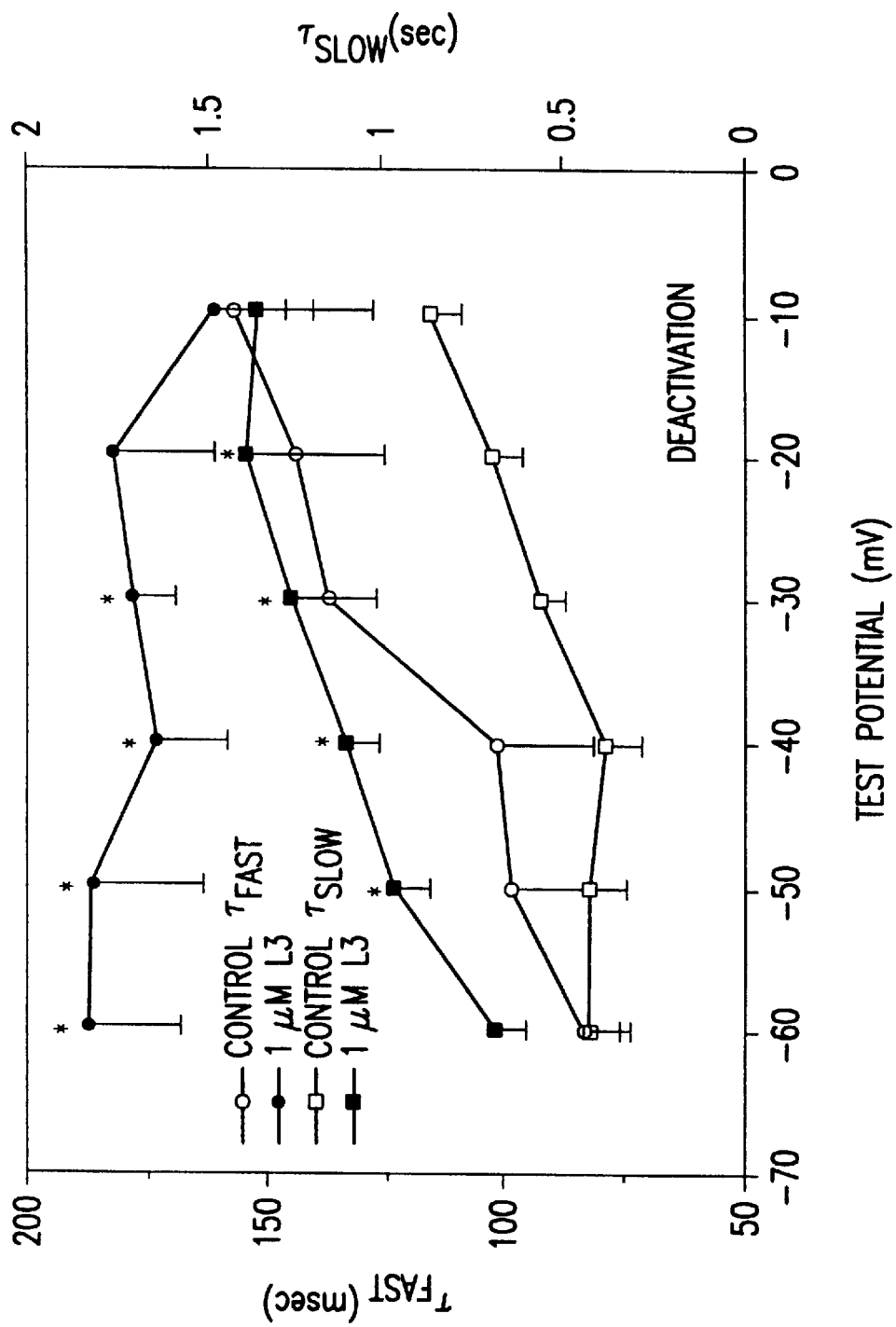
FIG. 4. R-L3 slows the rate of $I_{Ks}$ deactivation in guinea pig isolated ventricular myocytes. Time constants for deactivation were determined for tail currents upon return to a variable potential after a 3 s activating pulse from −50 to +30 mV (N≧4). *Significantly different from control (p<0.05) by paired t-test.

The onset of $I_{Ks}$ activation, following a short delay, was best described by a two exponential function. The fast time constants of activation were slightly, but not significantly, faster in the presence of 1 μM R-L3. This effect was likely due to the negative shift in the voltage dependence of channel activation. In contrast to the modest effect on the kinetics of activation, R-L3 greatly slowed the rate of $I_{Ks}$ deactivation (FIG. 3A). The kinetics of deactivation were determined at potentials of −60 to −10 mV following a 3 s pre-pulse to +30 mV from a $V_h$ of −50 mV. The deactivation of $I_{Ks}$ was best described by a two exponential function before and after addition of R-L3. R-L3 significantly increased the fast ($t_{fast}$) and the slow ($t_{slow}$) time constants of deactivation (FIG. 4). The slowing of the rate of deactivation by R-L3 represents an additional mechanism that would increase outward current during repolarization of a cardiac.

Figure 5B:
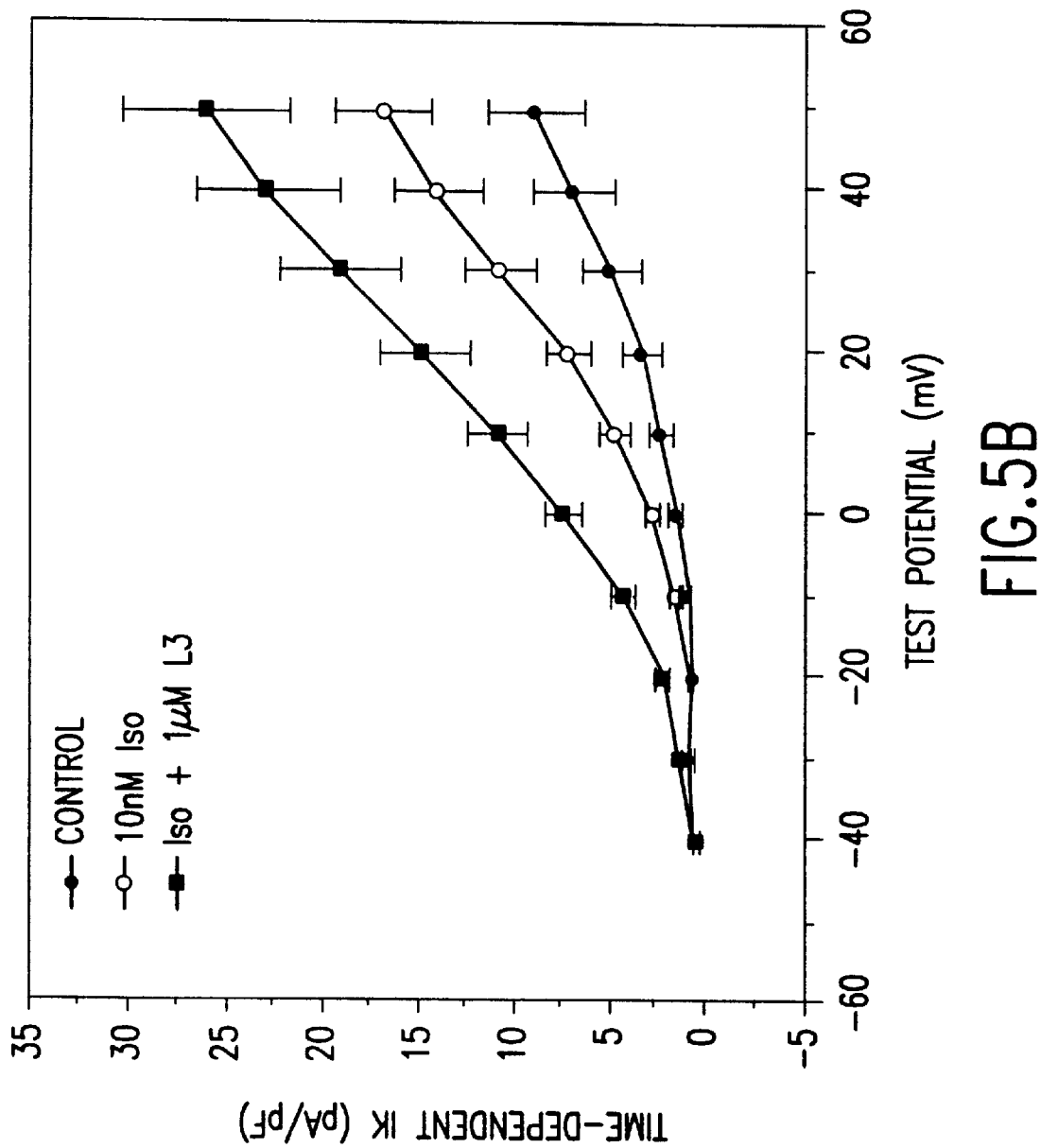
FIG. 5. Effects of Iso and R-L3, alone and in combination, on the Current-Voltage (I-V) relationship of $I_{Ks}$ in guinea pig isolated ventricular myocytes. A, Traces were recorded during control, after exposure to 10 nM Iso alone and after addition of 1 μM R-L3, then following washout of Iso but in the continued presence of R-L3. Currents were elicited by 0.5 s pulses from a $V_h$ of −50 mV. B I-V relationship for time-dependent $I_{Ks}$ for each condition (N=5).

R-L3 activates $I_{Ks}$ independent of β-adrenergic receptor activation. $I_{Ks}$ was activated by 0.5 s pulses to a $V_t$ ranging from −40 to +50 mV. Iso (10 nM) alone increased $I_{Ks}$ 1.75-fold. Addition of 1 μM R-L3 produced a further increase in $I_{Ks}$, slowed the rate of deactivation, and shifted the threshold for current activation to more negative potentials (FIG. 5). The effects of R-L3 persisted after washout of the Iso. Similar effects were observed when exposure of cells to R-L3 preceded the addition of Iso. Thus, similar to the decrease in APD caused by R-L3, the increase in $I_{Ks}$ by R-L3 was additive to that caused by β-adrenergic receptor stimulation.

Figure 6A:
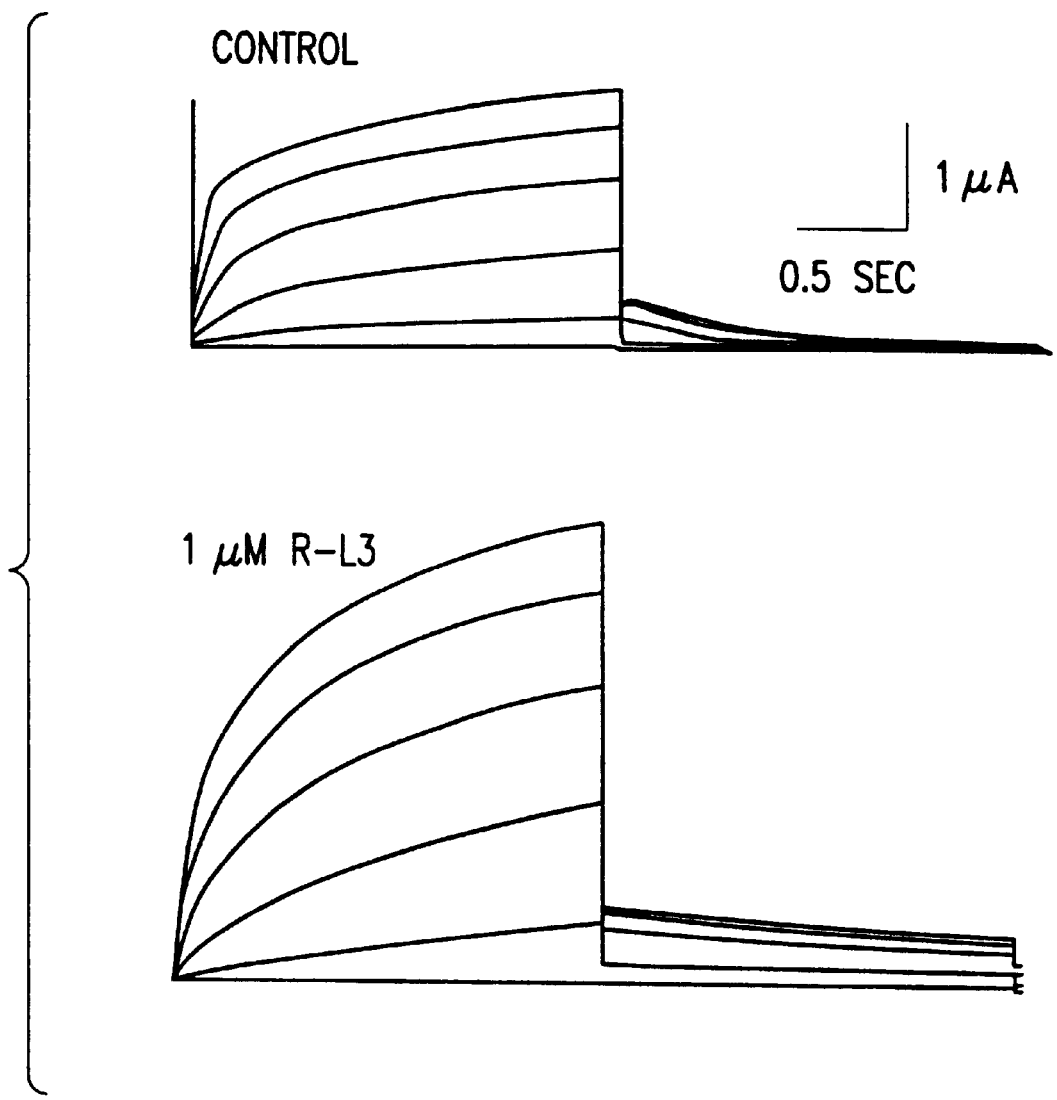
FIG. 6. R-L3 activates cloned KvLQT1 channels expressed in Xenopus oocytes. A, Currents were measured in response to 2 s pulses from a $V_h$ of −80 mV to a $V_t$ of −60 mV to +40 mV, applied in 20 mV increments. Tail currents were measured at −70 mV. B, Current-Voltage (I-V) relationships for peak KvLQT1 current during 2 s pulses to the indicated test potential before and after 1 μM. R-L3. C, Voltage-dependence of KvLQT1 activation. Tail current amplitudes were determined from extrapolating a single exponential fit of deactivating currents to the onset of membrane repolarization. Isochronal activation curves were determined by fitting normalized tail current amplitudes to a Boltzmann function. In control, the $V_{1/2}$ was −28 mV and the slope factor (k) was 11 mV for this relation. In the presence of 1 μM. R-L3, $V_{1/2}$ was −40 mV and k was 13 mV (N=8).
Figure 6B:
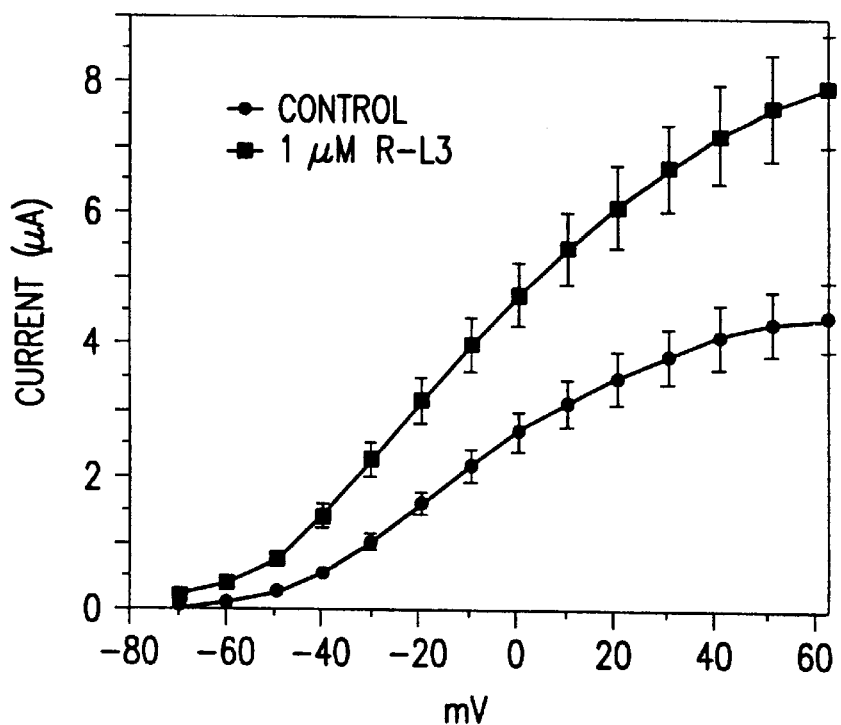
Figure 6C:
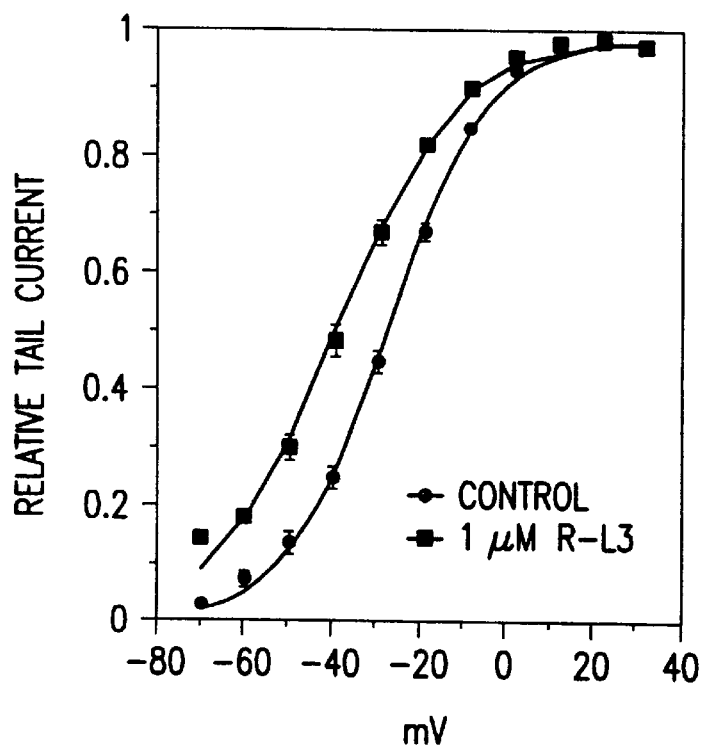
Figure 7A:
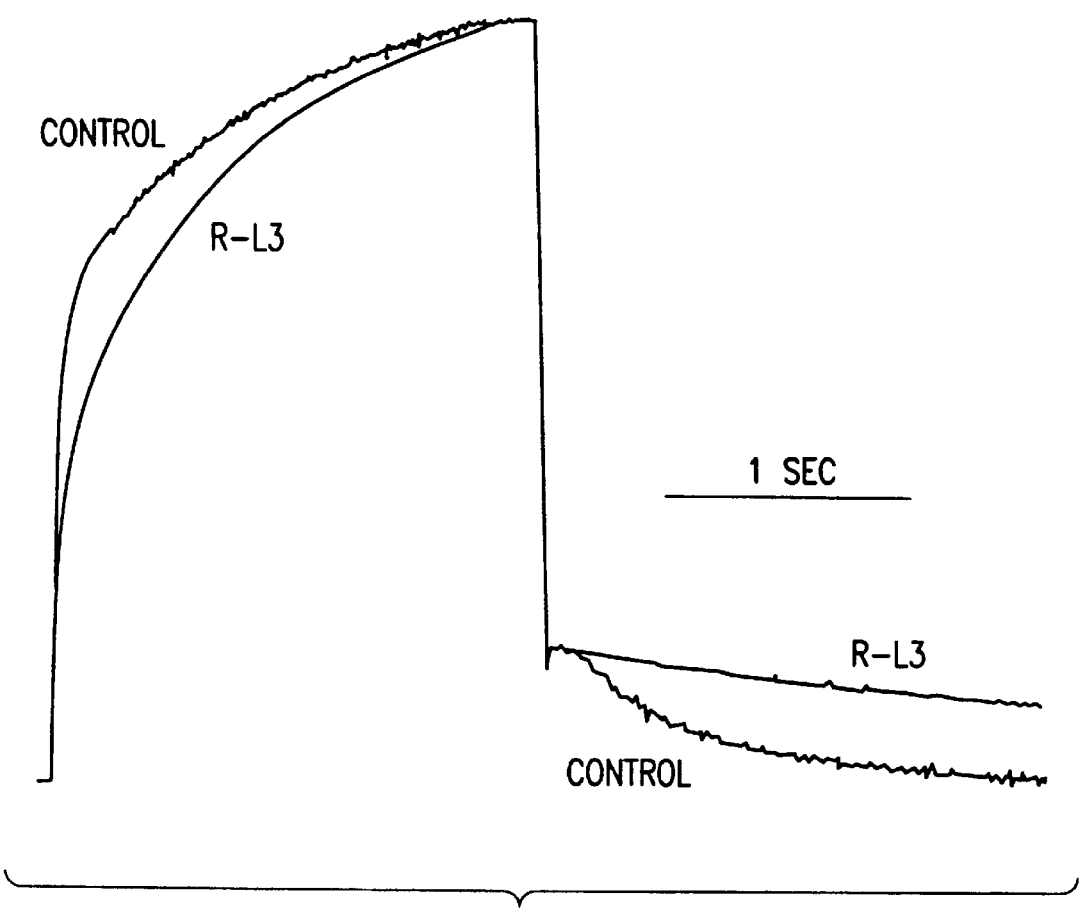
FIG. 7. R-L3 slows the rates of activation and deactivation of KvLQT1 expressed in Xenopus oocytes. A, To illustrate the change in KvLQT1 kinetics induced by R-L3, the peak current activated by a 2 s pulse to +40 mV was scaled to match the peak current recorded after addition of 1 μM . R-L3. Tail current was measured at −70 mV. B, Time constants for fast component of KvLQT1 activation. C, Time constants for slow component of KvLQT1 activation. D, Relative amplitude of the fast component of KvLQT1 activation. E, Time constants of KvLQT1 deactivation (N=8 for all graphs).
Figure 7B:
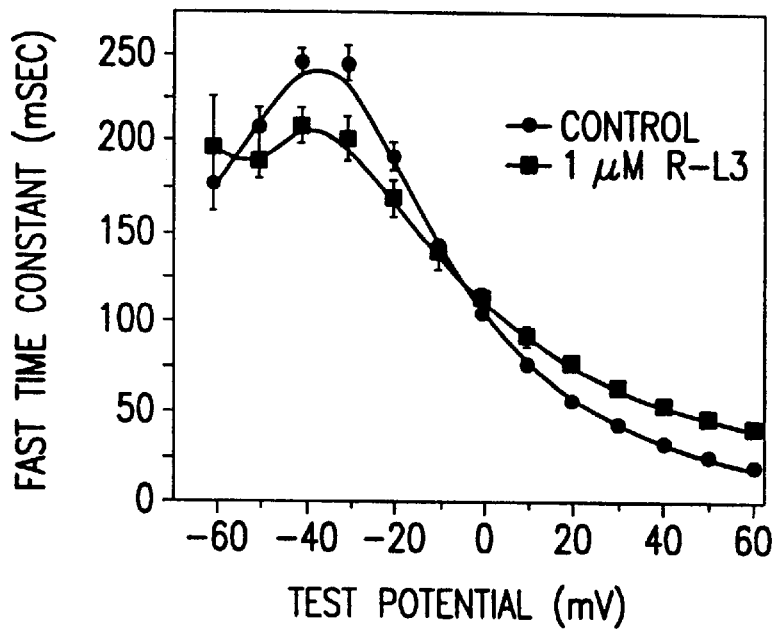
Figure 7C:
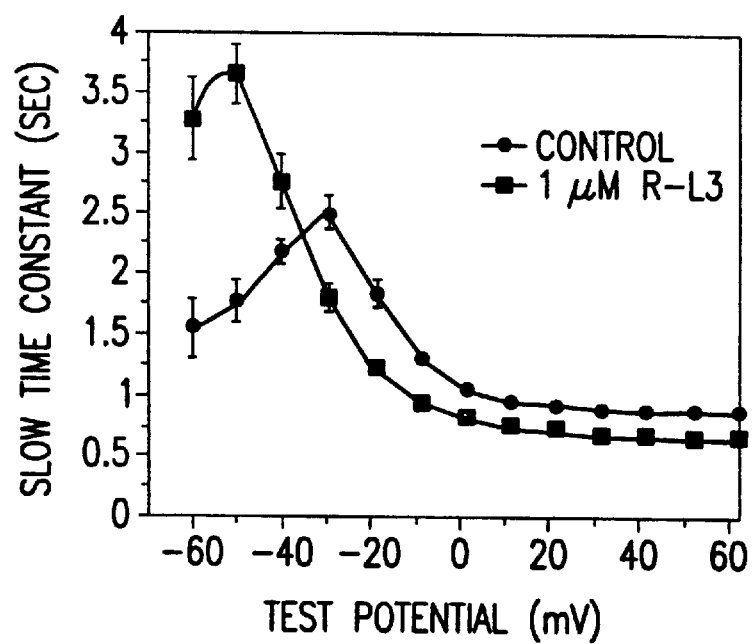
Figure 7D:
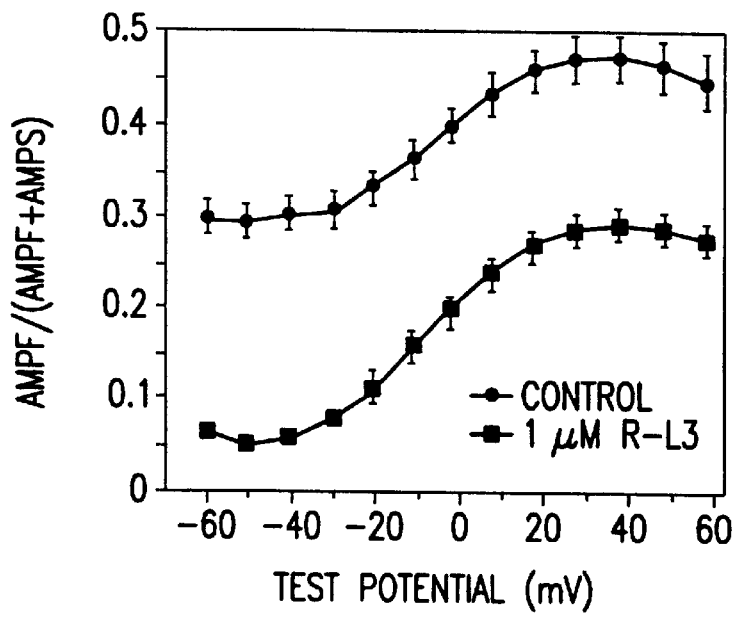
Figure 7E:
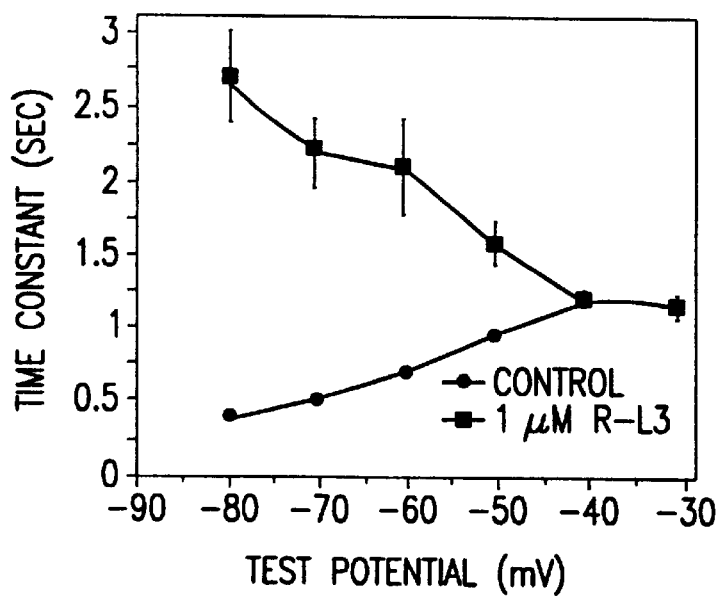

R-L3 activates cloned human KvLQT1 channels expressed in Xenopus oocytes. At a concentration of 1 μM, R-L3 increased KvLQT1 elicited with 2 s pulses to potentials ranging from −70 to +60 mV (FIGS. 6A, B). This increase can partially be accounted for by a −10 mV shift in the voltage dependence of activation caused by the drug (FIG. 6C). R-L3 also slowed the kinetics of KvLQT1, an effect that is easily observed when the time-dependent currents recorded before and after exposure to 1 μM R-L3 are superimposed and scaled to match peak current (FIG. 7A). Activation of KvLQT1 current is best described by a two exponential function. The effect of R-L3 on these two components varied with Vt. R-L3 slowed the rate of the fast component at $V_t \geq 0$ mV, (FIG. 7B), but increased the rate of the slow component of activation at $V_t \geq -30$ mV (FIG. 7C). The net effect of R-L3 was to slow the rate of KvLQT1 activation, because of a reduction in the relative amplitude of the fast component of activation over the entire voltage range that was examined (FIG. 7D). R-L3 also slowed the rate of KvLQT1 deactivation when assessed at voltages negative to −40 mV (FIG. 7E). Thus, R-L3 increased the magnitude of KvLQT1, shifted the voltage dependence of its activation, and slowed the rates of activation and deactivation. These effects of R-L3 on KvLQT1 current are similar to those observed for $I_{Ks}$ recorded in guinea pig ventricular myocytes.

Summary The properties of R-L3, a 1,4-benzodiazepin-2-one that selectively activates $I_{K_s}$ in myocytes at low concentrations are described in detail. At concentrations of 1 μM and less, R-L3 shortened action potential duration of cardiac myocytes by selective activation of $I_{K_s}$. At membrane potentials and pulse durations typical for a cardiac action potential, the most important mechanisms of action of R-L3 were a negative shift in the voltage dependence of activation, and a slowing of $I_{K_s}$ deactivation. R-L3 also caused a modest increase in $I_{K_s}$ beyond what could be explained by these two mechanisms. The molecular mechanism of these effects on $I_{K_s}$ channel gating is not clearly known, but it is not mediated through the β-adrenergic receptor activation pathway.

Dose Ranges

The magnitude of therapeutic dose of useful in this method of treatment will, of course, vary with the nature of, and the severity of the condition to be treated and with the particular compound utilized and its route of administration and pharmacokinetic profile and will vary upon the clinician's judgment. It will also vary according to the age, weight and response of the individual patient. An effective dosage amount of the active component can thus be determined by the clinician after a consideration of all the criteria and using is best judgment on the patient's behalf. Depending on these considerations, anticipated doses would be in the range of 0.1 μg/kg–10 mg/kg administered using an appropriate dosing regimen to maintain an effective plasma concentration.

Pharmaceutical Compositions

Any suitable route of administration may be employed for providing a mammal, especially a human with an effective dosage of a compound of the present invention. For example, oral, intraperitoneal, parenteral, subcutaneuous, intramuscular, transdermal, subkingual intravenous and topical may be employed. Dosage forms include tablets, troches, dispersions, suspensions, wafers, solutions, capsules, creams, ointments, aerosols, and the like.

The pharmaceutical compositions of a compound useful in the present method as an active ingredient or a pharmaceutically acceptable salt thereof, and may also contain a pharmaceutically acceptable carrier and optionally other therapeutic ingredients. The term "pharmaceutically acceptable salts" refers to salts prepared from pharmaceutically acceptable non-toxic bases or acids including inorganic bases or acids and organic bases or acids.

The compositions include compositions suitable for oral, parenteral. They may be conveniently presented in unit dosage form and prepared by any of the methods well-known in the art of pharmacy.

In practical use, the compounds exhibiting this activity can be combined as the active ingredient in intimate admixture with a pharmaceutical carrier according to conventional pharmaceutical compounding techniques. The carrier may take a wide variety of forms depending on the form of preparation desired for administration. In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, capsules and tablets, with the solid oral preparations being preferred over the liquid preparations. Because of their ease of administration, tablets and capsules represent the most advantageous oral dosage unit form in which case solid pharmaceutical carriers are obviously employed. If desired, tablets may be coated by standard aqueous or nonaqueous techniques.

Pharmaceutical compositions of the present invention suitable for oral administration may be presented as discrete units such as capsules, cachets or tablets each containing a predetermined amount of the active ingredient, as a powder or granules or as a solution or a suspension in an aqueous liquid, a non-aqueous liquid, an oil-in-water emulsion or a water-in-oil liquid emulsion. Such compositions may be prepared by any of the methods of pharmacy but all methods include the step of bringing into association the active ingredient with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation. For example, a tablet may be prepared by compression or molding, optionally with one or more accessory ingredients. Compressed tablets may be prepared by compressing in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Desirably, each tablet contains from about 1 mg to about 500 mg of the active ingredient and each cachet or capsule contains from about 1 to about 500 mg of the active ingredient.

The examples disclosed herein are representative of the instant invention, but should not be construed as limiting the scope of the invention.

EXAMPLES

The 1,4-benzodiazepin-2-ones of this invention can be prepared according to procedures described in U.S. Pat. No. 4,820,834, as well as the following literature references:

B. E. Evans et al. J. Med. Chem 1987, 30 pp. 1229–1239.
B. E. Evans et al. J. Med. Chem 1988, 31 pp. 2235–2246.
B. E. Evans et al. Proc. Natl. Acad. Sci. USA, Medical Sciences, July 1986, 83 pp.4918–4922.

The spiro[benzopyran-piperidine] compounds of this invention can be prepared according to procedures described in U.S. Pat. Nos. 5,206240 and 5,633,247.

Example 1

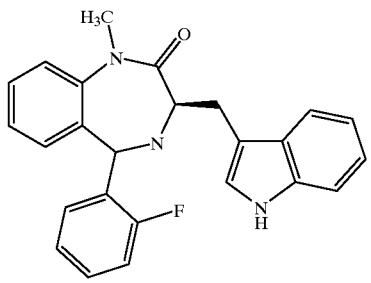

(3-R)-1,3-dihydro-5-(2-fluorophenyl)-3-(1H-indol-3-ylmethyl)-1-methyl-2H-1,4-benzodiazepin-2-one;

R-L3 was prepared as described previously by Evans et. al. (Evans BE, et al.J Med Chem 30: 1229–1239 (1987)). Its enantiomer, S-L3, was prepared by the same procedure described for R-L3, with L-tryptophan acid chloride hydrochloride used in place of the D-isomer: $^1$H-NMR (CDCl$_3$) identical to that of R-L3. The chemical and chiral purity of R-L3 and S-L3 were determined to be >99%. S-L3: HPLC (Vydac C-18, 15×0.46 cm, 16 min. gradient 95:5 to 5:95 0.1% H$_3$PO$_4$/H$_2$O:CH$_3$CN, 1.5 ml/min, 215 and 254 nM) retention time (rt)=11.0 min, >96%, co-elutes with R-L3. HPLC (Chiralcel OD, 25×0.46 cm, 90/10 hexane/EtOH, 1.5 ml/min, 280 nM) rt=9.95 min, 98.2%, contains <1% of R-L3 (R-L3: rt=10.94 min, 99.6%, contains <0.5% of S-L3). TLC (silica, 10% Et$_2$O in CH$_2$Cl$_2$): single component, Rf=0.43, co-elutes with R-L3. Calc. for C$_{25}$H$_{20}$FN$_3$O: C, 75.55; H, 5.07; N, 10.57; Found: C, 75.57; H, 5.17; N, 10.46.

Examples 2–4

Other specific examples of 1,4-benzodiazepin-2-one agonists are as follows:

R-L4

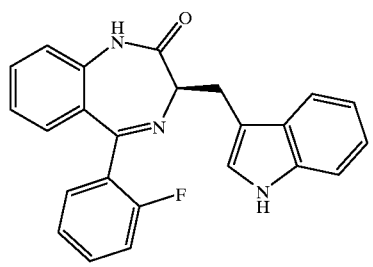

(3-R)-1,3-dihydro-5-(2-fluorophenyl)-3-(1H-indol-3-ylmethyl)-2H-1,4-benzodiazepin-2-one;

R-L5

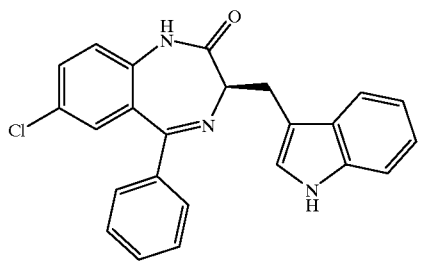

(3-R)-7-chloro-1,3-dihydro-5-phenyl-3-(1H-indol-3-ylmethyl)-2H-1,4-benzodiazepin-2-one; and

L6

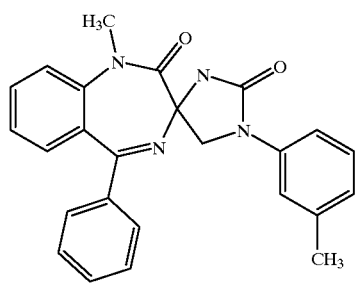

1-methyl-5-phenyl-1'-(3-tolyl)-spiro[3H-1,4-benzodiazepine-3,4'-imidazolidine]-2(1H),2',5'-trione

|  | Agonist Effect - % Increase in IKs | | |
|---|---|---|---|
| Compd. Ref. | Conc. [μM] | No. of runs | Vt −10 mV | Vt +50 mV |
| R-L3 | 0.1 | 6 | 431 ± 123 | 25 ± 6 |
|  | 1 |  | 1703 ± 507 | 40 ± 12 |
| R-L4 | 1 | 3 | 27 ± 7 | 44 ± 9 |
|  | 10 |  | 153 ± 37 | 114 ± 13 |
| R-L5 | 10 | 3 | 22 ± 10 | 22 ± 6 |
| L6 | 10 | 3 | — | 31 ± 9 |

Examples 5–6

Specific examples of spiro[benzopyran-piperidine] agonists are as follows:

L7

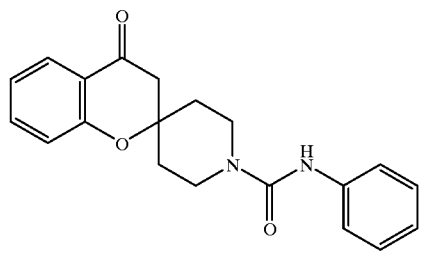

N-phenyl 1'-(carboxamido)-spiro[2H-1-benzopyran-2,4'-piperidin]-4(3H)-one; and

L8

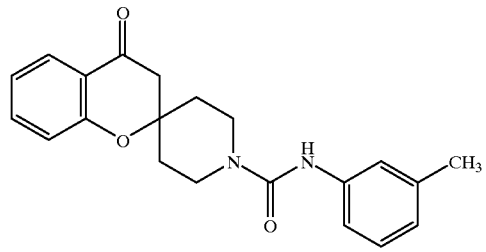

N-(3-tolyl) 1'-(carboxamido)-spiro[2H-1-benzopyran-2,4'-piperidin]-4(3H)-one.

|  | Agonist Effect - % Increase in IKs | | |
|---|---|---|---|
| Compd. Ref. | Conc. [μM] | No. of runs | Vt −10 mV | Vt +50 mV |
| L7 | 1 | 4 | no change | 111 ± 28 |
| L8 | 10 | 4 | no change | 65 ± 17 |

What is claimed is:

1. A method of treating cardiac ventricular arrhythmias and repolarization abnormalities associated with long QT syndrome and/or congestive heart failure comprising the adminstration of a therapeutically effective amount of an agonist of the slowly activating cardiac delayed rectifier potassium current (I$_{Ks}$) to a patient in need of such treatment.

2. The method as recited in claim 1, wherein the agonist of the slowly activating cardiac delayed rectifier potassium current (I$_{Ks}$) is a 1,4-benzodiazepin-2-one or a spiro [benzopyran-piperidine].

3. The method as recited in claim 2, wherein the agonist of the slowly activating cardiac delayed rectifier potassium current ($I_{Ks}$) is a (3-R)-3-(1H-indol-3-ylmethyl)-1,4-benzodiazepin-2-one.

4. The method as recited in claim 2 wherein the 1,4-benzodiazepin-2-one agonist of the slowly activating cardiac delayed rectifier potassium current ($I_{Ks}$) is selected from the group consisting of:

(3-R)-1,3-dihydro-5-(2-fluorophenyl)-3-(1H-indol-3-ylmethyl)-1-methyl-2H-1,4-benzodiazepin-2-one;

(3-R)-1,3-dihydro-5-(2-fluorophenyl)-3-(1H-indol-3-ylmethyl)-2H-1,4-benzodiazepin-2-one;

(3-R)-7-chloro-1,3-dihydro-5-phenyl-3-(1H-indol-3-ylmethyl)-2H-1,4-benzodiazepin-2-one; and 1-methyl-5-phenyl-1'-(3-tolyl)-spiro[3H-1,4-benzodiazepine-3,4'-imidazolidine]-2(1H),2',5'-trione, or pharmaceutically acceptable salts thereof.

5. The method as recited in claim 2, wherein the agonist of the slowly activating cardiac delayed rectifier potassium current ($I_{Ks}$) is a spiro[benzopyran-piperidine].

6. The method as recited in claim 2 wherein the spiro[benzopyran-piperidine] agonist of the slowly activating cardiac delayed rectifier potassium current ($I_{Ks}$) is selected from the group consisting of:

N-phenyl-1'-(carboxamido)-spiro[2H-1-benzopyran-2,4'-piperidin]-4(3H)-one; and

N-(3-tolyl)-1'-(carboxamido)-spiro[2H-1-benzopyran-2,4'-piperidin]-4(3H)-one, or pharmaceutically acceptable salts thereof.

7. A method for improving contractile dysfunction in a congestive heart failure patient comprising the adminstration of a therapeutically effective amount of an agonist of the slowly activating cardiac delayed rectifier potassium current ($I_{Ks}$) to a patient in need of such treatment.

8. The method as recited in claim 7, wherein the agonist of the slowly activating cardiac delayed rectifier potassium current ($I_{Ks}$) is a 1,4-benzodiazepin-2-one or a spiro[benzopyran-piperidine].

9. The method as recited in claim 8, wherein the agonist of the slowly activating cardiac delayed rectifier potassium current ($I_{Ks}$) is a (3-R)-3-(1H-indol-3-ylmethyl)-1,4-benzodiazepin-2-one.

10. The method as recited in claim 8 wherein the 1,4-benzodiazepin-2-one agonist of the slowly activating cardiac delayed rectifier potassium current ($I_{Ks}$) is selected from the group consisting of:

(3-R)-1,3-dihydro-5-(2-fluorophenyl)-3-(1H-indol-3-ylmethyl)-1-methyl-2H-1,4-benzodiazepin-2-one;

(3-R)-1,3-dihydro-5-(2-fluorophenyl)-3-(1H-indol-3-ylmethyl)-2H-1,4-benzodiazepin-2-one;

(3-R)-7-chloro-1,3-dihydro-5-phenyl-3-(1H-indol-3-ylmethyl)-2H-1,4-benzodiazepin-2-one; and 1-methyl-5-phenyl-1'-(3-tolyl)-spiro[3H-1,4-benzodiazepine-3,4'-imidazolidine]-2(1H),2',5'-trione, or pharmaceutically acceptable salts thereof.

11. The method as recited in claim 7, wherein the agonist of the slowly activating cardiac delayed rectifier potassium current ($I_{Ks}$) is a spiro[benzopyran-piperidine].

12. The method as recited in claim 8 wherein the spiro[benzopyran-piperidine] agonist of the slowly activating cardiac delayed rectifier potassium current ($I_{Ks}$) is selected from the group consisting of:

N-phenyl-1'-(carboxamido)-spiro[2H-1-benzopyran-2,4'-piperidin]-4(3H)-one; and

N-(3-tolyl)-1'-(carboxamido)-spiro[2H-1-benzopyran-2,4'-piperidin]-4(3H)-one, or pharmaceutically acceptable salts thereof.

* * * * *